(12) United States Patent
Hopper

(10) Patent No.: US 11,198,122 B2
(45) Date of Patent: Dec. 14, 2021

(54) DIAGNOSTIC TEST ASSEMBLY, APPARATUS, METHOD

(71) Applicant: AXXIN PTY LTD, Fairfield (AU)

(72) Inventor: William Hopper, East Ivanhoe (AU)

(73) Assignee: AXXIN PTY LTD, Fairfield (AU)

( * ) Notice: Subject to any disclaimer, the term of this patent is extended or adjusted under 35 U.S.C. 154(b) by 0 days.

(21) Appl. No.: 15/742,048

(22) PCT Filed: Jul. 15, 2016

(86) PCT No.: PCT/AU2016/050632
§ 371 (c)(1),
(2) Date: Jan. 5, 2018

(87) PCT Pub. No.: WO2017/011862
PCT Pub. Date: Jan. 26, 2017

(65) Prior Publication Data
US 2018/0193831 A1    Jul. 12, 2018

(30) Foreign Application Priority Data

Jul. 17, 2015 (AU) ................................. 2015902850

(51) Int. Cl.
*B01L 7/00* (2006.01)
*C12Q 1/686* (2018.01)
(Continued)

(52) U.S. Cl.
CPC ..... *B01L 3/50273* (2013.01); *B01L 3/502738* (2013.01); *B01L 7/52* (2013.01);
(Continued)

(58) Field of Classification Search
CPC ....... B01L 2300/123; B01L 2400/0481; B01L 2400/0655; B01L 2200/0689;
(Continued)

(56) References Cited

U.S. PATENT DOCUMENTS 4,234,540 A   11/1980 Ginsberg et al.
4,250,266 A   2/1981 Wade
(Continued)

FOREIGN PATENT DOCUMENTS

AU   2013202899 A1   5/2013
EP      1059523 B1   7/2007
(Continued)

OTHER PUBLICATIONS

Cone et al., "Protocol for Ultraviolet Irradiation of Surfaces to Reduce PCR Contamination," PCR Methods and Applications, vol. 3, pp. S15-S17 (Year: 1993).*
(Continued)

*Primary Examiner* — Young J Kim
(74) *Attorney, Agent, or Firm* — Shay Glenn LLP

(57) ABSTRACT

A diagnostic test assembly, including: a substrate having formed therein a plurality of mutually spaced open reservoirs and fluidic channels; a deformable membrane attached to the substrate to cover the open reservoirs and fluidic channels; a rigid covering disposed over the deformable membrane, the rigid covering being configured to allow respective actuators external to the diagnostic test assembly to displace corresponding portions of the deformable membrane; wherein at least some of the portions of the deformable membrane act as pumping portions, each pumping portion being disposed over a corresponding one of the reservoirs and being configured so that when it is displaced by a corresponding actuator, it is displaced into the corresponding reservoir to pump fluid from the corresponding reservoir through at least a corresponding one of the fluidic channels; and wherein one or more of the portions of the deformable membrane act as valve portions, each valve portion being configured so that when it is displaced, it blocks fluid flow through a corresponding reservoir or
(Continued)

fluidic channel; and wherein movement of fluid within the diagnostic test assembly can be controlled by controlling displacements of the portions of the deformable membrane.

19 Claims, 16 Drawing Sheets

(51) Int. Cl.
*B01L 3/00* (2006.01)
*F04B 43/00* (2006.01)

(52) U.S. Cl.
CPC .............. *C12Q 1/686* (2013.01); *F04B 43/00* (2013.01); *B01L 2200/0684* (2013.01); *B01L 2200/0689* (2013.01); *B01L 2200/16* (2013.01); *B01L 2300/0654* (2013.01); *B01L 2300/0672* (2013.01); *B01L 2300/123* (2013.01); *B01L 2400/0481* (2013.01); *B01L 2400/0655* (2013.01); *B01L 2400/0683* (2013.01)

(58) Field of Classification Search
CPC ......... B01L 2200/16; B01L 2400/0683; B01L 3/50273; B01L 3/502738; B01L 7/52; C12Q 1/686; F04B 43/00
See application file for complete search history.

(56) References Cited

U.S. PATENT DOCUMENTS

| | | | |
|---|---|---|---|
| 4,912,034 | A | 3/1990 | Kalra et al. |
| 5,152,965 | A | 10/1992 | Fisk et al. |
| 5,435,970 | A | 7/1995 | Mamenta et al. |
| 5,955,351 | A | 9/1999 | Gerdes et al. |
| 6,171,870 | B1 | 1/2001 | Freitag |
| 6,197,598 | B1 | 3/2001 | Schrier et al. |
| 7,238,520 | B2 | 7/2007 | Brown et al. |
| 8,895,296 | B2 | 11/2014 | Sano et al. |
| 9,757,095 | B2 | 9/2017 | Terbrueggen et al. |
| 9,932,629 | B2 | 4/2018 | Hopper |
| 2002/0031768 | A1 | 3/2002 | McMillan et al. |
| 2003/0129738 | A1 | 7/2003 | Sorenson et al. |
| 2003/0170686 | A1 | 9/2003 | Hoet et al. |
| 2004/0161788 | A1 | 8/2004 | Chen et al. |
| 2004/0265173 | A1 | 12/2004 | Matsumoto et al. |
| 2005/0033196 | A1 | 2/2005 | Alroy |
| 2005/0142031 | A1 | 6/2005 | Wickstead et al. |
| 2005/0180891 | A1* | 8/2005 | Webster .............. B01L 3/50273 422/505 |
| 2006/0030790 | A1 | 2/2006 | Braig et al. |
| 2006/0188392 | A1 | 8/2006 | Tanaka et al. |
| 2006/0223172 | A1 | 10/2006 | Bedingham et al. |
| 2006/0270027 | A1 | 11/2006 | Shaw et al. |
| 2006/0275852 | A1 | 12/2006 | Montagu et al. |
| 2006/0275922 | A1 | 12/2006 | Gould et al. |
| 2006/0292035 | A1 | 12/2006 | Gould et al. |
| 2007/0184492 | A1 | 8/2007 | Wang et al. |
| 2008/0020380 | A1 | 1/2008 | Patno et al. |
| 2008/0166820 | A1 | 7/2008 | Gould et al. |
| 2008/0199851 | A1 | 8/2008 | Egan et al. |
| 2008/0287308 | A1 | 11/2008 | Hubbell et al. |
| 2009/0181388 | A1 | 7/2009 | You et al. |
| 2009/0204997 | A1 | 8/2009 | Xu et al. |
| 2011/0039261 | A1 | 2/2011 | Hillebrand et al. |
| 2011/0283818 | A1 | 11/2011 | Kramer |
| 2012/0076693 | A1 | 3/2012 | Hopper |
| 2013/0309679 | A1* | 11/2013 | Ismagilov .......... C12N 15/1003 435/6.12 |
| 2014/0194305 | A1* | 7/2014 | Kayyem ........... B01L 3/502738 506/9 |
| 2014/0377766 | A1 | 12/2014 | Hopper |
| 2015/0024436 | A1 | 1/2015 | Eberhart et al. |
| 2015/0190805 | A1 | 7/2015 | Etheredge et al. |
| 2016/0258849 | A1 | 9/2016 | Murayama et al. |
| 2017/0318802 | A1 | 11/2017 | Hopper et al. |
| 2019/0376129 | A1 | 12/2019 | Hopper |

FOREIGN PATENT DOCUMENTS

| | | | | |
|---|---|---|---|---|
| EP | 2123360 | A1 | 11/2009 | |
| EP | 2163999 | A2 | 3/2010 | |
| FR | 2590673 | A1 | 5/1987 | |
| JP | H08-43294 | A | 2/1996 | |
| WO | WO92/08986 | A1 | 5/1992 | |
| WO | WO99/57561 | A2 | 11/1999 | |
| WO | WO-2004011148 | A2 * | 2/2004 | .......... F04B 43/1223 |
| WO | WO 2005/045408 | A1 | 5/2005 | |
| WO | WO2006/047777 | A2 | 5/2006 | |
| WO | WO2007/005077 | A1 | 1/2007 | |
| WO | WO2007/106579 | A2 | 9/2007 | |
| WO | WO2008/005248 | A2 | 1/2008 | |
| WO | WO 2009/011869 | A1 | 1/2009 | |
| WO | WO 2009/132268 | A1 | 10/2009 | |
| WO | WO2010/030686 | A1 | 3/2010 | |
| WO | WO2010/104478 | A1 | 9/2010 | |
| WO | WO2013/113054 | A1 | 8/2013 | |
| WO | WO-2014000037 | A1 * | 1/2014 | ............ B01L 3/5023 |
| WO | WO2014/100732 | A1 | 6/2014 | |
| WO | WO2015/084458 | A2 | 6/2015 | |
| WO | WO-2015084458 | A2 * | 6/2015 | .......... B01L 3/50273 |
| WO | WO2017/062892 | A1 | 4/2017 | |

OTHER PUBLICATIONS

Cikos et al.; Transformation of real-time PCR fluorescence data to target gene quantity; Analytical Biochemistry; 384(1); pp. 1-10; Jan. 1, 2009.
Durtschi et al.; Evaluation of quantification methods for real-time PCR minor groove binding hybridization probe assays; Analytical Biochemistry; 361(1); pp. 55-64; Jan. 4, 2007.
European Leukemia Network; Imatinib testing for CML; 7 pages; retrieved from the internet (https://www.eutos.org/content/molecular_monitoring/information/pcr_testing/index_eng.html); on Apr. 4, 2018.
Gubala et al.; Point of care diagnostics: status and future; Analytical Chemistry; 84(2); pp. 487-515; Jan. 2012.
Liu et al.; Progress curve analysis of qRT-PCR reactions using the logistic growth equation; Biotechnology Progress; 27(5); pp. 1407-1414; Sep. 15, 2011.
Pipper et al.; Clockwork PCR including sample preparation; Angew. Chem. Int. Ed.; 47(21); pp. 3900-3904; Apr. 15, 2008.
Roche Diagnostics GMBH; LightCycler 480 Instrument Operator's Manual, Software version 1.5; © 2008; 8 pages; Oct. 15, 2014; retrieved from the internet (http://pedrovale.files.wordpress.com/2013/08/lightcyclerc2ae-480-instrument-operators-manual.pdf).
Wikipedia; Immunoassay; 4 pages; Feb. 24, 2015; retrieved from the internet (http://en.wikiopedia.org/wiki/Immunoassay).
Wikipedia; Lateral flow test; 4 pages; Feb. 24, 2015; retrieved from the internet (http:en.wikipedia.org/wiki/Lateral_flow_test).
Wikipedia; Polymerase chain reaction; 13 pages; Oct. 15, 2014; retrieved from the internet (http://en.wikipedia.org/wiki/Polymerase_chain_reaction).
Wikipedia; Variants of PCR; 11 pages; Oct. 15, 2014; retrieved from the internet (http://en.wikipedia.org/wiki/Variants_of_PCR#Isothermal_amplification_methods).
Zhang et al.; Micropumps, microvalves, and micromixers within pcr microfludic chips: Advances and trends; Biotechnology Advances; 25(5); pp. 483-514; Sep. 1, 2007.
Hopper; U.S. Appl. No. 16/650,125 entitled "Diagnostic test system and method," filed Mar. 24, 2020.

* cited by examiner

DIAGNOSTIC TEST ASSEMBLY, APPARATUS, METHOD

TECHNICAL FIELD

The present invention relates to a diagnostic test assembly, a diagnostic test apparatus, and a diagnostic test method for performing diagnostic tests or analysis of samples to aid in environmental, agricultural, scientific, veterinary or medical diagnosis based on detection of the presence or absence of specific analytes in a sample and determining its quantity in the sample. The analyte may be detected using methods of molecular DNA amplification and detection of specific genetic markers.

BACKGROUND

The amplification of nucleic acids is important in many fields, including medical, biomedical, environmental, veterinary and food safety testing. In general, nucleic acids are amplified by one of two methods: polymerase chain reaction (PCR) or isothermal amplification, both of which are described below.

Polymerase Chain Reaction (PCR)

As described in the Wikipedia[1]:

"The polymerase chain reaction (PCR) is a scientific technique in molecular biology to amplify a single or a few copies of a piece of DNA across several orders of magnitude, generating thousands to millions of copies of a particular DNA sequence.

Developed in 1983 by Kary Mullis, PCR is now a common and often indispensable technique used in medical and biological research labs for a variety of applications. These include DNA cloning for sequencing, DNA-based phylogeny, or functional analysis of genes; the diagnosis of hereditary diseases; the identification of genetic fingerprints (used in forensic sciences and paternity testing); and the detection and diagnosis of infectious diseases. In 1993, Mullis was awarded the Nobel Prize in Chemistry along with Michael Smith for his work on PCR.

The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions.

PCR Principles and Procedure

PCR is used to amplify a specific region of a DNA strand (the DNA target). Most PCR methods typically amplify DNA fragments of up to ~10 kilo base pairs (kb), although some techniques allow for amplification of fragments up to 40 kb in size. A basic PCR set up requires several components and reagents. These components include:

DNA template that contains the DNA region (target) to be amplified.

Two primers that are complementary to the 3' (three prime) ends of each of the sense and anti-sense strand of the DNA target.

Taq polymerase or another DNA polymerase with a temperature optimum at around 70° C.

Deoxynucleoside triphosphates (dNTPs; nucleotides containing triphosphate groups), the building-blocks from which the DNA polymerase synthesizes a new DNA strand.

Buffer solution, providing a suitable chemical environment for optimum activity and stability of the DNA polymerase.

Divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis.

Monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures required at each step of the reaction (see below). Many modern thermal cyclers make use of the Peltier effect, which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube. Older thermocyclers lacking a heated lid require a layer of oil on top of the reaction mixture or a ball of wax inside the tube.

Procedure

Typically, PCR consists of a series of 20-40 repeated temperature changes, called cycles, with each cycle commonly consisting of 2-3 discrete temperature steps, usually three . . . . The cycling is often preceded by a single temperature step (called hold) at a high temperature (>90° C.), and followed by one hold at the end for final product extension or brief storage. The temperatures used and the length of time they are applied in each cycle depend on a variety of parameters. These include the enzyme used for DNA synthesis, the concentration of divalent ions and dNTPs in the reaction, and the melting temperature (Tm) of the primers.

Initialization step: This step consists of heating the reaction to a temperature of 94-96° C. (or 98° C. if extremely thermostable polymerases are used), which is held for 1-9 minutes. It is only required for DNA polymerases that require heat activation by hot-start PCR.

Denaturation step: This step is the first regular cycling event and consists of heating the reaction to 94-98° C. for 20-30 seconds. It causes DNA melting of the DNA template by disrupting the hydrogen bonds between complementary bases, yielding single-stranded DNA molecules.

Annealing step: The reaction temperature is lowered to 50-65° C. for 20-40 seconds allowing annealing of the primers to the single-stranded DNA template. Typically the annealing temperature is about 3-5 degrees Celsius below the Tm of the primers used. Stable DNA-DNA hydrogen bonds are only formed when the primer sequence very closely matches the template sequence. The polymerase binds to the primer-template hybrid and begins DNA synthesis.

Extension/elongation step: The temperature at this step depends on the DNA polymerase used; Taq polymerase has its optimum activity temperature at 75-80° C., and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to be amplified. As a rule-of-thumb, at its optimum temperature, the DNA polymerase will polymerize a thousand bases per minute. Under optimum conditions, i.e., if there are no limitations due to limiting substrates or reagents, at each extension step, the amount of DNA target is doubled, leading to exponential (geometric) amplification of the specific DNA fragment.

Final elongation: This single step is occasionally performed at a temperature of 70-74° C. for 5-15 minutes after the last PCR cycle to ensure that any remaining single-stranded DNA is fully extended.

Final hold: This step at 4-15° C. for an indefinite time may be employed for short-term storage of the reaction.

PCR Stages

The PCR process can be divided into three stages:

Exponential amplification: At every cycle, the amount of product is doubled (assuming 100% reaction efficiency). The reaction is very sensitive: only minute quantities of DNA need to be present.

Leveling off stage: The reaction slows as the DNA polymerase loses activity and as consumption of reagents such as dNTPs and primers causes them to become limiting.

Plateau: No more product accumulates due to exhaustion of reagents and enzyme.

PCR Optimization

In practice, PCR can fail for various reasons, in part due to its sensitivity to contamination causing amplification of spurious DNA products. Because of this, a number of techniques and procedures have been developed for optimizing PCR conditions. Contamination with extraneous DNA is addressed with lab protocols and procedures that separate pre-PCR mixtures from potential DNA contaminants. This usually involves spatial separation of PCR-setup areas from areas for analysis or purification of PCR products, use of disposable plasticware, and thoroughly cleaning the work surface between reaction setups. Primer-design techniques are important in improving PCR product yield and in avoiding the formation of spurious products, and the usage of alternate buffer components or polymerase enzymes can help with amplification of long or otherwise problematic regions of DNA. Addition of reagents, such as formamide, in buffer systems may increase the specificity and yield of PCR.

Amplification and Quantification of DNA

Because PCR amplifies the regions of DNA that it targets, PCR can be used to analyze extremely small amounts of sample. This is often critical for forensic analysis, when only a trace amount of DNA is available as evidence. PCR may also be used in the analysis of ancient DNA that is tens of thousands of years old. These PCR-based techniques have been successfully used on animals, such as a forty-thousand-year-old mammoth, and also on human DNA, in applications ranging from the analysis of Egyptian mummies to the identification of a Russian tsar. Quantitative PCR methods allow the estimation of the amount of a given sequence present in a sample—a technique often applied to quantitatively determine levels of gene expression. Real-time PCR is an established tool for DNA quantification that measures the accumulation of DNA product after each round of PCR amplification.

PCR in Diagnosis of Diseases

PCR permits early diagnosis of malignant diseases such as leukemia and lymphomas, which is currently the highest-developed in cancer research and is already being used routinely. PCR assays can be performed directly on genomic DNA samples to detect translocation-specific malignant cells at a sensitivity that is at least 10,000-fold higher than that of other methods.

PCR also permits identification of non-cultivatable or slow-growing microorganisms such as mycobacteria, anaerobic bacteria, or viruses from tissue culture assays and animal models. The basis for PCR diagnostic applications in microbiology is the detection of infectious agents and the discrimination of non-pathogenic from pathogenic strains by virtue of specific genes.

Viral DNA can likewise be detected by PCR. The primers used need to be specific to the targeted sequences in the DNA of a virus, and the PCR can be used for diagnostic analyses or DNA sequencing of the viral genome. The high sensitivity of PCR permits virus detection soon after infection and even before the onset of disease. Such early detection may give physicians a significant lead in treatment. The amount of virus ("viral load") in a patient can also be quantified by PCR-based DNA quantitation techniques (see below).

Isothermal Amplification Methods

As described in the Wikipedia[1]:

"Some DNA amplification protocols have been developed that may be used alternatively to PCR:

Helicase-dependent amplification is similar to traditional PCR, but uses a constant temperature rather than cycling through denaturation and annealing/extension steps. DNA Helicase, an enzyme that unwinds DNA, is used in place of thermal denaturation.

PAN-AC also uses isothermal conditions for amplification, and may be used to analyze living cells.

Nicking Enzyme Amplification Reaction referred to as NEAR, is isothermal, replicating DNA at a constant temperature using a polymerase and nicking enzyme.

Recombinase Polymerase Amplification (RPA). The method uses a recombinase to specifically pair primers with double-stranded DNA on the basis of homology, thus directing DNA synthesis from defined DNA sequences present in the sample. Presence of the target sequence initiates DNA amplification, and no thermal or chemical melting of DNA is required. The reaction progresses rapidly and results in specific DNA amplification from just a few target copies to detectable levels typically within 5-10 minutes. The entire reaction system is stable as a dried formulation and does not need refrigeration. RPA can be used to replace PCR (Polymerase Chain Reaction) in a variety of laboratory applications and users can design their own assays.

Detection of Genetic Targets within a Test Sample.

After DNA amplification there will be a large number of copies of the target genetic sequences in the test solution. In a diagnostic test assay, specific markers can be designed that will link to the target sequences, and once bonded provide an optical signal or optical change that can be detected external to the test tube. This optical signal may be a change in the colour and/or opacity of the sample as measured by a change in the optical absorption of the sample at specific optical wavelengths. The output signal may also be by way of direct light output from the sample, where the marker, when activated by target bonding event, triggers release of bioluminescence light output. The optical detection output may also be by a change in the fluorescence of the solution, which may be from a fluorescence marker beacon. In this case, each marker molecule is configured with a florescence quencher in close proximity to a fluorescence atom or arrangement of atoms.

This marker molecule is configured such that when it selectively binds to a target DNA sequence in the test solution, the quencher and fluorophore are separated and a strong fluorescence signal can then be detected by the action of the fluorophore. In this arrangement, the overall florescence intensity of the target solution is indicative of the relative amount of target generic material in the test solution. This signal can them be used to form the basis of a diagnostic test to determine the presence or absence and the relative quantity of the target material in the sample under test.

Control Channel and Multiplexing.

Within a single test well, it is possible to have several different markers present that will provide an optical output based on bonding to several different target genetic DNA sequences. In this case several different sensors are used or a sensor with more than one selective output is used. For example in a two channel system, two different fluorescence markers may be employed, and these will be detected by two different fluorescence sensors configured to detect emissions in respective frequency ranges specific to the respective fluorescence markers to allow the channels to be discriminated.

This approach can be used to provide a control channel where the test assay chemistry is configured such that the control target should always be present if the test process is run correctly. In this case, the output of the control channel is used to confirm that the test process has been run correctly by the system, and to confirm that test results obtained by other channels measured by the system are valid.

This approach can be also used to test for more than one target genetic sequence within each test well as a multiplexed test.

Multiple test wells may be used, with each well running differently configured amplification chemistry and a different set of target markers. Control channels may operate in one or more wells and cover tests operated other wells in the test. By this arrangement a number of tests can be conducted on a single sample as a different approach to multiplexing.

Existing nucleic acid amplification and detection apparatus are typically large, complex and costly.

It is desired to provide a diagnostic test assembly, apparatus and method that alleviate one or more difficulties of the prior art, or that at least provide a useful alternative.

SUMMARY

In accordance with some embodiments of the present invention, there is provided a diagnostic test assembly, including:
  a substrate having formed therein a plurality of mutually spaced open reservoirs and fluidic channels;
  a deformable membrane attached to the substrate to cover the open reservoirs and fluidic channels;
  a rigid covering disposed over the deformable membrane, the rigid covering being configured to allow respective actuators external to the diagnostic test assembly to displace corresponding portions of the deformable membrane;
  wherein at least some of the portions of the deformable membrane act as pumping portions, each pumping portion being disposed over a corresponding one of the reservoirs and being configured so that when it is displaced by a corresponding actuator, it is displaced into the corresponding reservoir to pump fluid from the corresponding reservoir through at least a corresponding one of the fluidic channels;
and
  wherein one or more of the portions of the deformable membrane act as valve portions, each valve portion being configured so that when it is displaced, it blocks fluid flow through a corresponding reservoir or fluidic channel; and
  wherein movement of fluid within the diagnostic test assembly can be controlled by controlling displacements of the portions of the deformable membrane.

In some embodiments, the diagnostic test assembly of claim 1, wherein the rigid covering disposed over the deformable membrane has openings through which the external actuators can pass to apply pressure to corresponding portions of the deformable membrane.

In some embodiments, the rigid covering has displaceable portions connected to other portions of the covering by one or more corresponding deformable attachment regions, each said displaceable portion being displaceable to move from an initial position to at least one displaced position that correspondingly deforms a corresponding portion of the deformable membrane.

In some embodiments, the reservoirs include a sample input reservoir configured to receive a sample for analysis within the diagnostic test assembly.

In some embodiments, that least a first one of the reservoirs contains reagents for sample preparation including cell lysis, and at least a second one of the reservoirs is configured for nucleic acid amplification and binding of specific markers to provide an optical output that can be measured by one or more sensors external to the diagnostic test assembly to determine a diagnostic test result.

In some embodiments, the diagnostic test assembly includes a plurality of test reservoirs containing dried or lyophilized test reagents, wherein the displaceable portions of the rigid covering include test reservoir displaceable portions configured to disrupt seals of the test reservoirs when moved to respective first displaced positions to allow fluid to flow into the test reservoirs from at least one corresponding fluid channel, and to then seal the volume of fluid contents within the well when moved to respective second displaced positions.

In some embodiments, at least one of the reservoirs contains a sealed sachet of liquid, and the corresponding displaceable portion of the rigid covering is configured to disrupt the sachet to release the liquid into the reservoir when the corresponding displaceable portion is moved into the reservoir to a displaced position.

In some embodiments, the corresponding displaceable portion of the rigid covering is configured to disrupt the sachet to release the liquid into the reservoir when the corresponding displaceable portion is moved to a first displaced position, and to seal the reservoir when moved to a second displaced position.

In some embodiments, the diagnostic test assembly includes a deformable plug or cap disposed over at least one of the test wells, and configured to redirect fluid entering the test well towards a base of the test well to inhibit bubble formation or capture in the test well during filling of the test well.

In some embodiments, the fluidic channels include at least one input channel for filling the test reservoirs and at least one output channel to receive fluid from the test reservoirs, at least one spatial dimension of the at least one output channel being smaller than at least one spatial dimension of the at least one input channel such that fluid flow from the test reservoirs to the at least one output channel is inhibited until the test reservoirs have been filled.

In accordance with some embodiments of the present invention, there is provided a diagnostic test apparatus, including:
  a housing having a receiving port configured to receive any one of the above diagnostic test assemblies;
  a controller; and
  a plurality of actuators configured to selectively displace respective ones of the portions of the deformable membrane under control of the controller to selectively control the movement of fluid within the diagnostic test assembly.

In some embodiments, the controller is configured to cause at least one of the actuators to repeatedly displace a corresponding portion of the deformable membrane between first and second positions and thereby to cause mixing of contents of a corresponding reservoir of the diagnostic test assembly.

In some embodiments, the diagnostic test apparatus includes a heater block configured to heat the test reservoirs within the assembly for iso-thermal or thermo-cycling PCR nucleic acid amplification.

In some embodiments, the diagnostic test apparatus includes one or more image sensors configured to generate image data representing one or more images of at least one portion of the diagnostic test assembly, wherein the images represent at least one of: (i) at least one identifier that identifies the diagnostic test assembly; and (ii) the fluid distribution within at least some of the channels and reservoirs to allow the controller to monitor, confirm or control the status and action of cartridge actuations.

In some embodiments, the at least one identifier identifies a corresponding diagnostic test to be applied to the diagnostic test assembly and determining at least one of the actuation of the actuators and the thermal processing of one or more of the reservoirs.

In some embodiments, the diagnostic test apparatus includes one or more optical sensors configured to generate optical data representing optical absorption or emission by a sample in one or more of the test reservoirs.

In some embodiments, the one or more optical sensors are mounted to a translation stage under control of the controller so that the optical sensors can measure optical absorption or emission from selected reservoirs of the diagnostic test assembly.

In some embodiments, the diagnostic test apparatus includes at least one ultra violet (UV) emission source as a denaturing component configured to denature samples contained within the diagnostic test assembly following a diagnostic test to inhibit contamination in the event of sample fluid escaping from the diagnostic test assembly.

In accordance with some embodiments of the present invention, there is provided a diagnostic test process, including:
  receiving any one of the above diagnostic test assemblies;
  selectively displacing each of the portions of the deformable membrane to a corresponding displaced position to selectively pump fluid through reservoirs and fluidic channels of the diagnostic test assembly to test wells of the diagnostic test assembly for analysis.

Also described herein is an instrument apparatus, including:
  an instrument housing with an access port that will accept a plastic cartridge assembly.
  an image sensor such as a CMOS image sensor or charge coupled device where this sensor consists of a plurality of pixels that can register the intensity of incident light and form an image of part or all of the inserted cartridge.
  an illumination source consisting of a plurality of light emitting diodes or other electrically excited illumination sources.
  optical diffusers that can assist in evenly distributing the illumination across the area of the cartridge to be imaged.
  reference targets within the field of view of the image sensor and the illumination source.
  A sensor or switch that will detect the insertion or presence of the cartridge inserted into the apparatus.
  controller electronics and associated internal electronics, microprocessor and memory that will run a software program and save data for future recall and use.
  Electrical interface connectors for connection of USB, serial or Ethernet connected peripherals interfaces and external memory devices.
  embedded software to provide functions to sequence processing of the instrument, the cartridge and acquire diagnostic test measurements for interpretation determination of test outcome.
  actuators that can apply pressure onto the cartridge at specific locations to progress fluid movements within the test cartridge.
  a temperature controlled heater block that will contact specific test wells in an inserted cartridge where this block can apply controlled temperatures including temperature cycling to fluids within the cartridge wells.

Sensors that will detect and provide measurement of optical absorption, fluorescence or bioluminescence within the test wells during the course of the test running and at the completion of the test reactions.

Also described herein is a test cartridge device, including:

a moulded plastic carrier supporting a plastic tray, this tray configured with depressions that are loaded with liquid, powdered, dried or lyophilized reagents.

grooves in the tray to form fluid communication channels between the of processing depressions in the tray and fluid connections to allow filling of a set of test wells.

a deformable membrane bonded across the top surface of the tray such that the tray depressions with included reagents form cavities and the groves in the tray form enclosed channels connecting the cavities. The channels formed by the tray and the overlaying bonded membrane form a method to move fluids between the depressions and features moulded into the tray.

a rigid top cover that protects the deformable membrane and the contained test reagents within the tray depressions during storage and transport prior to use in a diagnostic test.

a number of rigid island regions in the moulded plastic top cover positioned over the membrane covered depressions in the underlying tray. The perimeter of these rigid island regions in the top cover are each surrounded by weakened, removed or reduced thickness material.

each rigid island region of the top cover configured such that the weakened perimeter of the region will distort or collapse and the island region will be pressed down when an electrical or pneumatic actuator mounted within the instrument presses press down onto that region. When each rigid island region in the top cover is pressed down with sufficient force by the associated actuator, the underside of the region will come into contact with and deform the membrane covering the associated tray depression. This action will displace fluid from within the depression into a connected channel and transfer this fluid and any reagents mixed with the fluid to other cavities within the tray.

one or more valve locations where an actuator can press down on a section of the deformable membrane and press the membrane down into a flattened section of one of the fluid communication grooves such the channel is closed and will not allow fluid to flow.

a plurality of test wells formed within a separate plastic component. These wells containing dried or lyophilized test reagents and protected by a bonded foil cover. This component fixed in contact with the cartridge tray such the once the foil cover is perforated, the enclosed wells will be in fluid communication with the depressions in the test tray and can be filled with test fluids displaced from the tray regions under the action of sequenced actuators.

the test wells in the cartridge contact with a heater block within the instrument. This contact allowing the well contents to at a controlled temperature to facility the test reaction for iso-thermal or thermo-cycling PCR nucleic acid amplification.

sachets or capsules of liquid reagents placed within specific depressions in the tray.

dried or lyophilized reagents placed within specific depressions in the tray.

wells or locations within the tray configured to allow mixing and reaction times for reagents a sample in-put port that will allow a solid or liquid sample to be introduced into the cartridge.

a rigid island section of the top cover positioned over the test well strip. This section of the top cover constructed with a weakened perimeter and downward directed projections. This section of the top cover configured such that when it is partially depressed by actuators in the instrument the projections will perforate the foil cover of the test well strip and allow displaced fluids from the tray to flow into the test wells. This section of the top cover also configured such that and when fully depressed by the instrument actuators the projections incorporate a larger diameter plug and will fully seal the test wells with a volume of displaced test reagent fluid captured within each well cavity.

Optionally, a metallic or thermally conductive block in contact with the test wells provides a controlled temperature under electronic control using a single or multitude of feedback temperature sensors mounted on the block. This heated block configured to heat and control the temperature of the fluid contents of the test wells through the plastic well walls for the purposes of obtaining a test reaction including iso-thermal or PCR nucleic acid, DNA amplification.

Optionally, a metallic or thermally conductive block is in contact with the cartridge tray fluid volumes provides a controlled temperature under electronic control using a single or multitude of feedback temperature sensors mounted on the block. This block configured to heat the internal test fluids through the cartridge tray walls to a known temperature for the purposes of sample preparation and cell lysis prior to flow into the test wells.

Optionally, the temperature sensors can include one or more Infrared emission non-contact temperature sensors, where these sensor can be configured to read the block temperature or the actual temperature of the fluid in the reaction test wells.

Optionally, the instrument apparatus incorporates one or more optical sensors where these sensors can be scanned along a row of test wells to allow a multitude of measurement to be recoded for each test well using one or more different sensors.

Optionally, one or more of the sensors is a coaxial fluorescence sensor where optically filtered emissions from a light emitting diode, or laser illumination of a selective wavelength range is emitted from the sensor lens. This illumination will cause optical excitation of the sample in the test well and the same lens will also capture florescence emission from the sample at a different shifted wavelength. This sample fluorescence emission is measured and forms a measurement used in determining the diagnostic test result.

Optionally, one or more of the sensors will detect fluorescence within the sample contained within each test well using a separated excitation illumination source to optically excite the test sample and a separated sensor to measure the resulting fluorescence emission.

Optionally, one or more of the sensors will use reflectance or transmission of specific optical illumination wavelength ranges to measure optical reflectance or absorption within the test sample contained within each test well.

Optionally, one or more of the sensors will measure light emission from the test sample where this emission is caused by luminescence or bio-luminescence within the test sample.

Optionally, the sensors are scanned at constant speed past all of the wells and a multitude of measurements acquired. Subsequent processing of this data set of measurements can determine the measurement values to assign to each test well. This analysis to consider such characteristics as the relative position or the acquisition time of each measurement and local peaks with an interpolated curve encompassing the acquired measurements.

Optionally, the instrument apparatus incorporates one or more ultraviolet light sources, where this ultraviolet illumination can be turned on or off by the instrument controller. This ultraviolet illumination used to decontaminate and denature the contents of the test cartridge including the contents of the test wells at the completion of a test.

Optionally, the ultraviolet illumination is used to breakdown and genetic nucleic acid products including the products of nucleic acid amplification within each test well at the completion of the test. This denaturing and breakdown of genetic DNA material by ultraviolet illumination to prevent any contamination of the system or its environment by amplicons if the cartridge is subsequently damaged, or leaks and to prevent this material inadvertently being introduced into a subsequent test and causing an erroneous test result.

Optionally, the ultraviolet illumination is carried along with the detection sensors on a carriage that can mechanically scan along a multitude of test wells. This arrangement allowing a single focused ultraviolet source to illuminate each well in turn during a controlled de contamination scan.

Optionally, the ultraviolet source is made up of one or more ultraviolet light emitting diodes.

Optionally, the flexible deformable membrane is a plastic sheet selectively welded to mating surfaces on the moulded plastic tray.

Optionally, during the manufacture process the flexible membrane is retained on a roll and is pulled off this roll onto a second roll forming a web between these two rolls. The web located such that it passed across the station where trays will be positioned during welding. The welding operation being performed by a press system which will selectively weld, perforate and cut the outer outline of the membrane from the web in each welding operation.

Optionally, a row of one or more test wells is formed in a separate moulded plastic component such that it can be processed, filled with reagents including lyophilized reagents and sealed by a bonded foil cover in a separate processing flow prior to final assembly of the complete cartridge.

Optionally, sections of the protective top cover has regions to allow the membrane in that section to be depressed by actuators in the instrument apparatus. The membrane when depressed into an underlying well in the tray will positively displace fluids within the well through interconnecting channels to other connected wells. By successively depressing the covering membrane into wells, and holding them depressed, the fluid can be caused to progress through a series of wells to allow processing the test reagents and causing the diagnostic test to operate.

Optionally, the top cover has regions with reduced strength or thickness such that the region can be collapsed or depressed with sufficient pressure to cause deflection of the flexible membrane mounted under the cover into specific wells in the tray.

Optionally, regions in the top cover have weakened edges with reduced thickness or with material removed such that the reduced interconnecting plastic will deform or rupture under the actuator pressure to allow the plastic of the cover region to be depressed onto the underlying membrane and displacing fluid volume in the underlying tray well.

Optionally, the deformable region is elongated and two actuators can act on its surface. The weakened retaining perimeter of this region will allow each end of the region to break away but allow a central region to stay attached forming pivot if only a single actuator is extended to depress one end of the region. If a single actuator is depressed at each end in turn, the top cover will seesaw depressing only one end of the membrane covered well region at a time. This action will cause mixing within the contained test fluid.

Optionally, a set of optical measurement sensors can view the test well contents through an optical widow or port in the test well and its surrounding heater block and produce measurements of optical absorption, florescence or bioluminescence.

Optionally, the optical sensors are mounted on carriage that that can me moved linearly along the test wells to scan the and provide an optical measurement for each well in a set of wells.

Optionally, the linear scan is performed by the carriage at a constant speed and the peak reading or an average of readings associated with each test well is assigned as that the optical reading for each well.

Optionally, the carriage moves on a linear slide arrangement that can be driven by a stepper motor to provide accurate position and motion control under software control and electrical interface to the instrument controller.

Optionally, a set of reference samples are mounted within the instrument such the sensors used to acquire well measurements can also acquire measurements of the reference samples.

Optionally, a specific set of sensor measurements acquired when measuring the reference samples are saved to a non volatile memory location within the instrument controller such that these saved readings can be used in the future to confirm that subsequent readings are within a given tolerance range of the saved readings for each respective sensor and reference sample.

Optionally, the capability to compare the sensor readings of the reference materials mounted within the instrument against previously saved readings for the same sample for the purposes of the instrument controller performing an instrument self test.

Optionally, code marks or a bar code or a two dimensional code such as QR code is printed on the surface of the cartridge assembly.

Optionally, the coded marks are printed by laser marking, lase discoloration or laser etching on the plastic surface of the cartridge.

Optionally, the image sensor incorporated within the instrument in combination with the illumination incorporated within the instrument can acquire an image of a printed code on the cartridge and through a process of image analysis in software, extract the encoded information.

Optionally, the information encoded within the printed code includes one or more of following data, the test identification, details of the test sequence and temperatures to be applied to run the cartridge, a unique cartridge serial number, the manufacturing batch number for the cartridge, batch specific calibration parameters, the manufacture date of the cartridge and an expiry date after which the cartridge should not be used.

Optionally, the image sensor can be used to confirm the sequence progression and correct release and flow of test reagents within the cartridge such that the integrity of the test can be confirmed by the software and used to improve the reliability and safety of the test result.

Optionally, the liquid reagent is coloured by a visual dye and the test output is a fluorescent signal, such that the reagent coloring does not interfere with the test output but this colour can be used to visually track flow within the cartridge.

Optionally, the image sensor within the instrument described in claim 1 can capture images of the colored reagent within transparent sections of the cartridge and confirm in software image analysis that particular flow requirements have operated correctly.

Optionally, a test sample is introduced into the cartridge and the cartridge inserted into the instrument. The cartridge depressions and test wells configured to contain the reagents necessary for sample preparation including cell lysis and following this nucleic acid amplification and binding of specific markers with an optical output that can be measured by the instrument sensors, where measurement of these optical maker outputs will allow the instrument to display a diagnostic test result.

Cartridge wells held closed.

Optionally, the cartridge incorporates the chemical and biological reagents required for sample preparation and nucleic acid amplification, genetic sequence binding and optical output using iso thermal nucleic acid amplification methods.

Optionally, the cartridge incorporates the chemical and biological reagents required for sample preparation and nucleic acid amplification and genetic sequence detection using polymerase chain reaction, PCR, nucleic acid amplification methods.

BRIEF DESCRIPTION OF THE DRAWINGS

Some embodiments of the present invention are hereinafter described, by way of example only, with reference to the accompanying drawings, wherein.

DETAILED DESCRIPTION

Embodiments of the present invention include a diagnostic test assembly (also referred to herein as a 'cartridge') and a diagnostic test apparatus (or 'instrument') that together constitute a diagnostic test system that is easy for a user to operate without requiring the facilities of a general test laboratory. In the described embodiments, the diagnostic test assembly is provided in the form of a disposable test cartridge that is produced prior to a test and already incorporates all of the precursor chemical components referred to as reagents to run a specific set of diagnostic tests. The cartridge is configured so that it can be safely handled without interfering with these chemical components or otherwise affecting the subsequent operations of the cartridge, which require interactions with the diagnostic test instrument.

Details of the cartridge and the diagnostic test apparatus or instrument are described below. By loading specific amplification and marker reagents into the cartridge, the system can be configured to run a specific set of diagnostic tests. Different versions of the cartridge can be produced to cover a wide range of test types and diagnostic applications.

The diagnostic test apparatus receives the cartridge and manipulates it through the specific sequence of sample addition, reagent release, dilution, mixing, temperature control and optical output sensing steps to determine a diagnostic test result and display or otherwise provide it as an output to a user. The cartridge protects the reagents in transport and storage prior to running a test, and supports the test process while the test is run.

The test reagents, amplification genetic products and contaminants are retained within the cartridge at the completion of the test. The cartridge can be removed for disposal at the completion of a test, and the instrument is protected from fluids and contamination.

Figure 1:
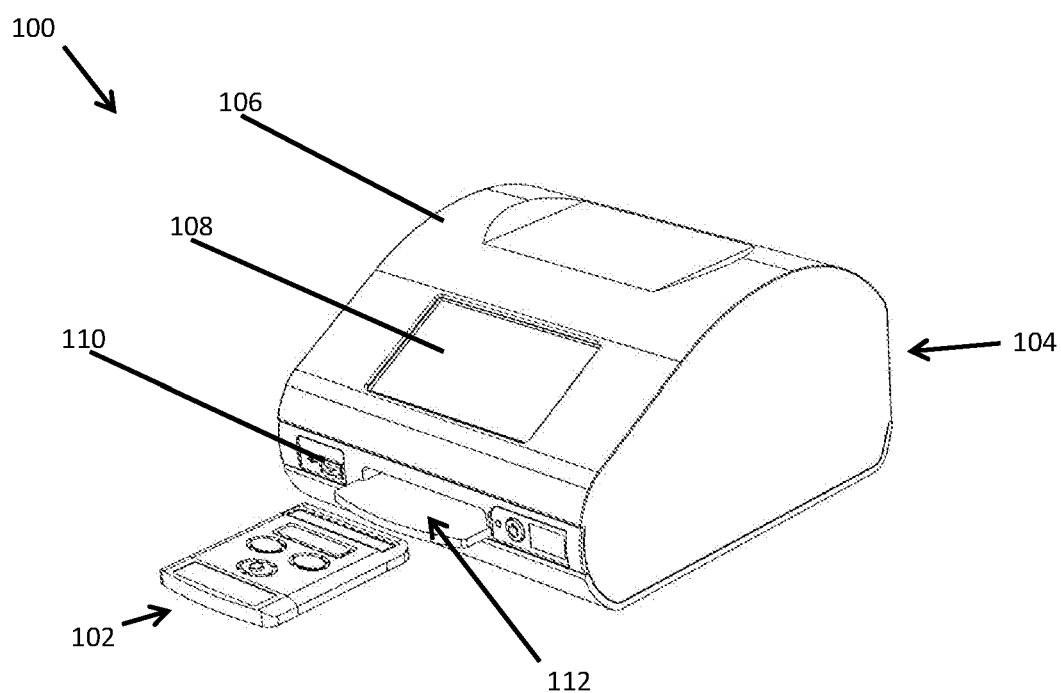
FIG. 1 is an illustration of a diagnostic test system consisting of a diagnostic test assembly or cartridge and a diagnostic test apparatus or instrument.
Figure 2:
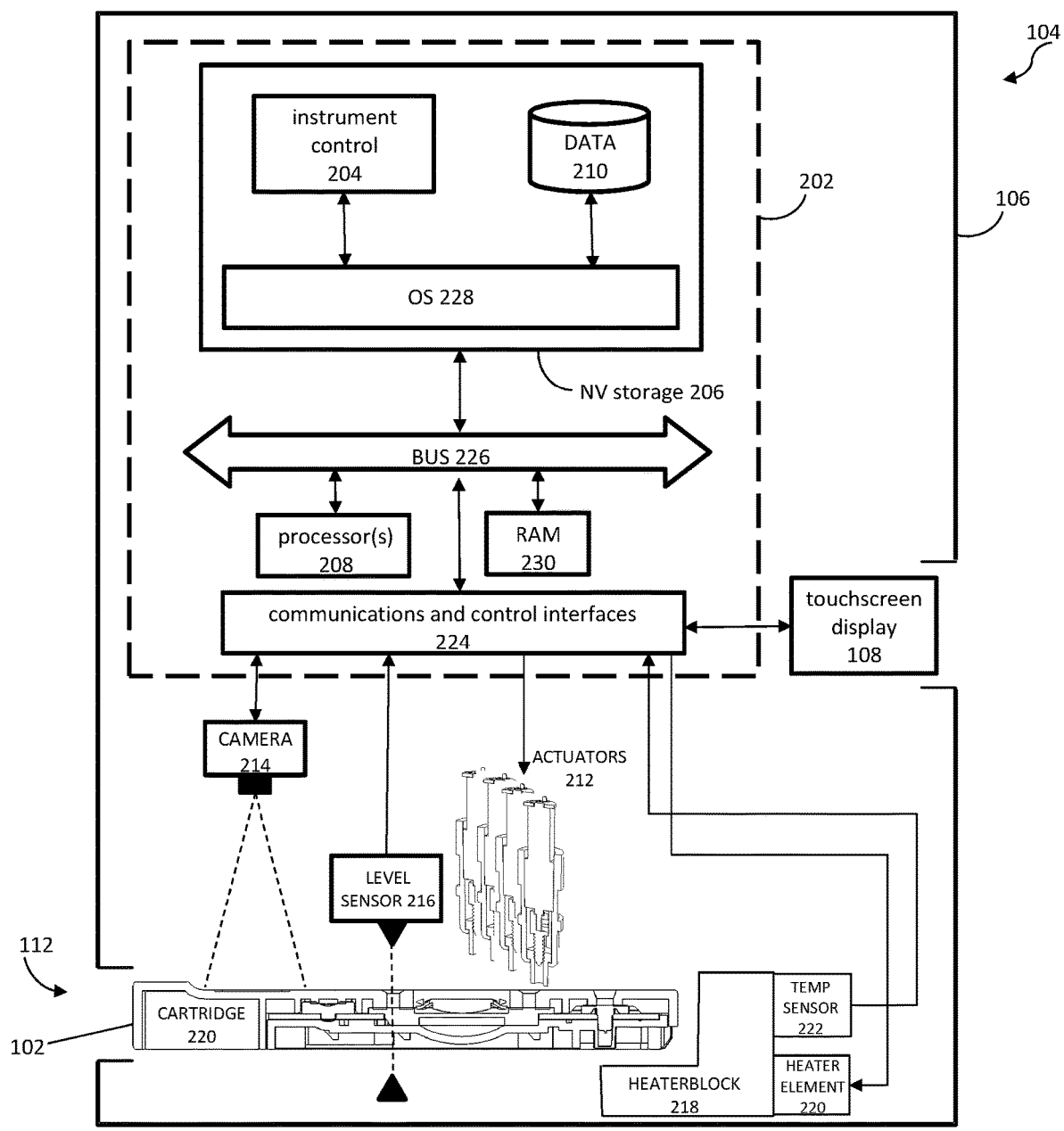
FIG. 2 is a block diagram of the diagnostic test apparatus or instrument of FIG. 1.

As shown in FIG. 1, a diagnostic test system 100 includes a diagnostic test assembly or cartridge 102 and a diagnostic test apparatus or instrument 104. As shown in FIGS. 1 and 2, the diagnostic test instrument includes a rigid enclosure or housing 106, which may be constructed from moulded plastic or metallic sheet materials. Within this housing 106, a touch sensitive LCD display 108 is mounted.

The instrument 104 is operated by selecting touch sensitive controls of a user interface (not shown) rendered on the instrument display 108, however in other embodiments the user interface may be implemented as physical controls or buttons to implement corresponding functions such as start test or keypad data entry.

As shown in FIG. 2, the instrument 104 incorporates a microprocessor-based controller 202 configured to execute diagnostic test processes that control the sequencing and operation of the instrument's electrically operated functions. In the described embodiment, the controller 202 is configured by way of embedded software 204 stored in non-volatile memory 206 in communication with at least one processor 208, as will be well understood by those skilled in the art. However, it will be apparent to those skilled in the art that some or all of the steps of the diagnostic test processes performed by the diagnostic test apparatus or instrument 104 can alternatively be implemented in other forms, such as configuration data for a field-programmable gate array (FPGA), or entirely in hardware form, such as an application-specific integrated circuit (ASIC), for example.

The non-volatile memory 206 also stores test results and instrument calibrations as data 210 stored in one or more data files or a database, and all of the information/data stored in the non-volatile memory 206 is retained, even when no power is provided to the diagnostic test instrument 104.

The instrument 104 also includes additional components external to and in communication with the controller 202, including a set of independently controllable actuators 212, an imaging sensor or camera 214, a level sensor 216, and a heater block 218 whose temperature is controlled by a heater element 220 and temperature sensor 222. All of these components are interfaced to the controller 202 by way of communications and control interfaces 224, including USB and wired and wireless Ethernet interfaces, via a shared bus 226 and I/O functions of an operating system (OS) 228. The processor(s) 208 are also in communication with random access memory (RAM) 230, which is used to temporarily store processor instructions and data.

The instrument 104 also includes external data communication interface connectors, including a USB type A connector 110 shown in FIG. 1. Although not visible from the generally front-facing view of FIG. 1, additional rear mounted USB and Ethernet connectors and a power input connection are provided on the rear surface of the instrument 104. These data connections and an additional internal wifi wireless connections allow the instrument to communicate test results saved in its internal memory to external users and remote database storage.

The instrument 104 has a cartridge receiving port 112 that allows a diagnostic test cartridge 102 to be inserted into the instrument 104 for processing. The insertion of a cartridge 102 into the cartridge receiving port 112 is detected by cartridge presence sensors (not shown) located within the cartridge receiving port 112. In some embodiments, the cartridge presence sensors are based on optical detectors, whereas the described embodiment uses mechanical switches. Mechanical detents provide force feedback to the user and also locate the cartridge 102 in a stable and known location within the instrument 104.

Figure 3:
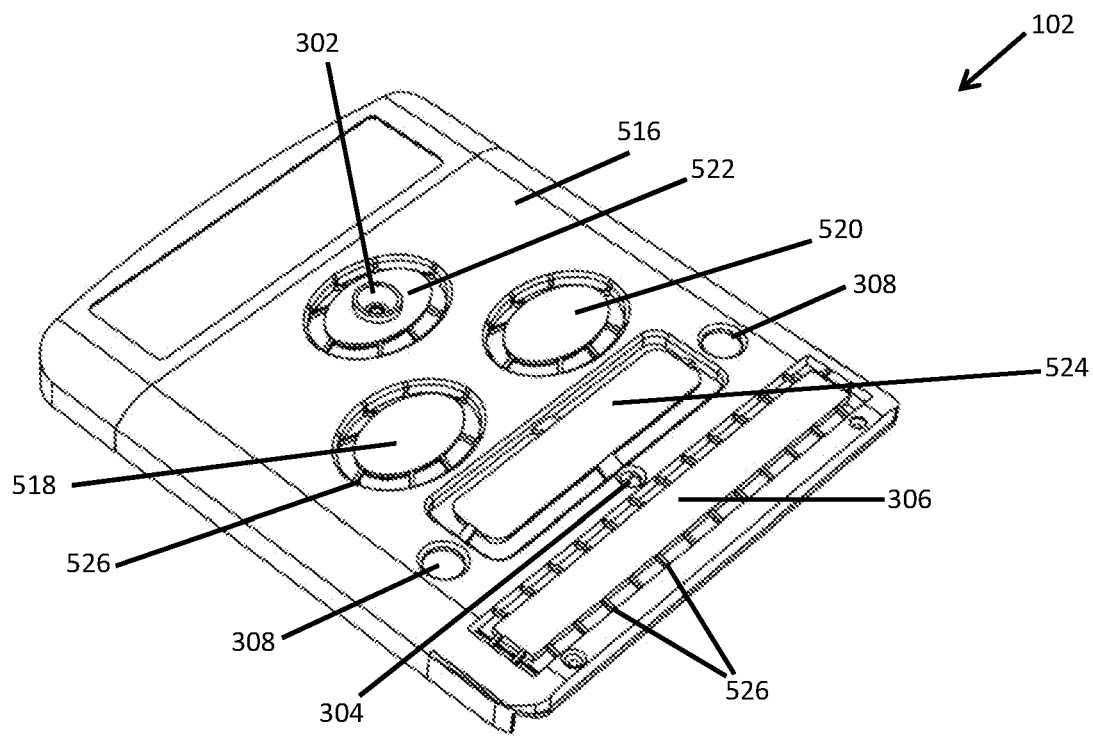
FIGS. 3 to 5 are different views of the diagnostic test assembly or cartridge of FIG. 1.
Figure 23:
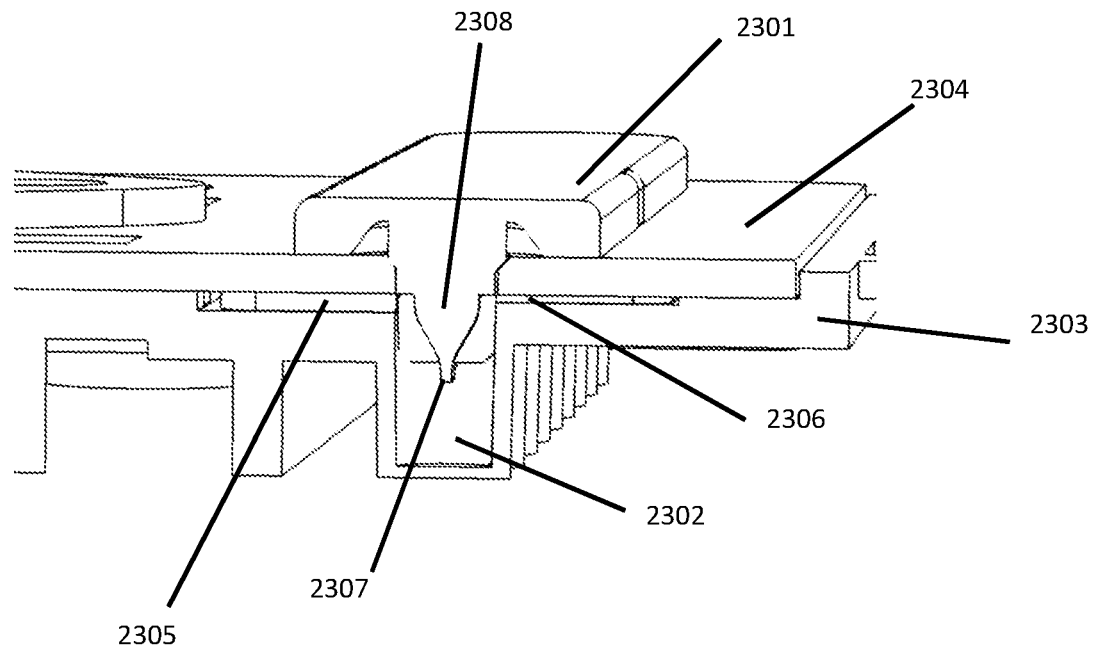
FIGS. 23 and 24 are diagrams illustrating the use of a deformable plug component to selective open or block input and output channels of a test well.

In the described embodiment, an initial detent position is provided corresponding to the cartridge 102 being fully supported by the instrument 104, but not fully inserted such that a sample input port 302 of the cartridge 102, as shown in FIG. 3, is still externally exposed and accessible. A mechanical switch detects the cartridge in this initial insertion position, which is indicative of a new diagnostic test, and causes the instrument controller to execute a diagnostic test process, as shown in FIG. 23, and provide by audio or visual display on the instrument display 108 prompts or instructions to the user. The instrument 104 begins preparation for the new test by bringing the internal temperature controlled heater block 218 up to a predetermined temperature for the test at step 2304, and at step 2306 the operator is prompted to add a test sample into the cartridge 102. When the instrument 104 detects this addition, and/or the user confirms that this has been done, the instrument 104 raises the internal actuators and any clamping elements away from the cartridge receiving port 112 to allow the cartridge 102 to be fully inserted into the instrument 104. The operator is then able to push the cartridge 102 fully into the instrument 104 until it locates securely into the fully inserted detent location.

The apparatus 104 includes flexible spring clips (not shown) to retain the cartridge 102 in location once fully inserted. In the described embodiment, the cartridge 102 has small depressions at one end to receive the clip assembly and provide a detent insertion feedback to the user, where an initial insertion resistance is overcome by the user, and then the cartridge clips fully into place where it is held securely with rounded tips of the spring clips sitting in corresponding depressions of the cartridge 102.

Cartridge Identification

Figure 4:
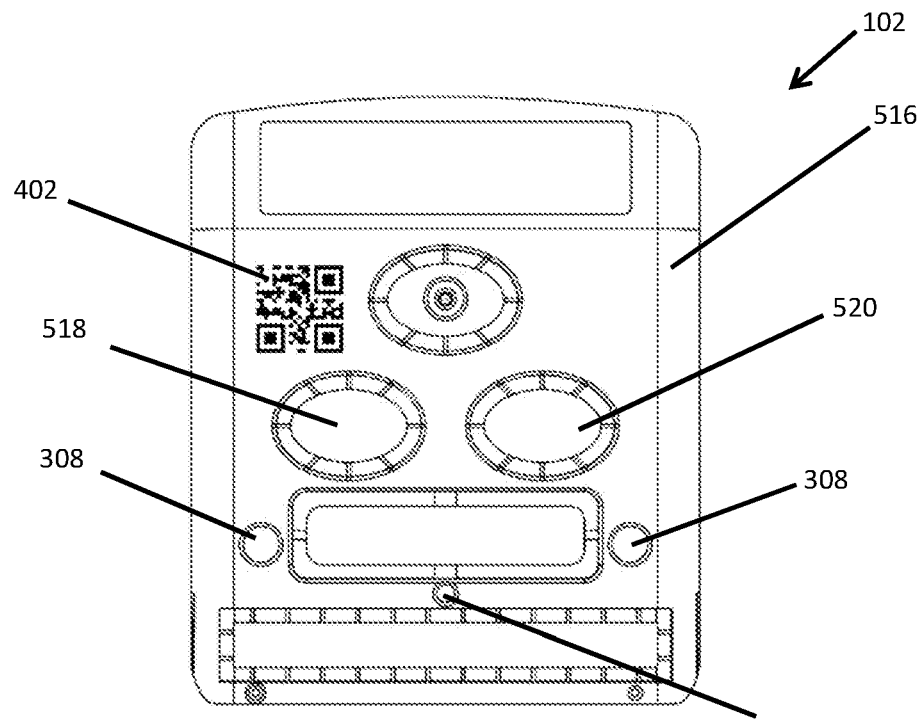

The diagnostic test system 100 can be configured to process different cartridge types in different ways, with different cartridge types being identified by identifiable marks or labels such as linear barcodes or 2D codes printed or etched onto the surface of the cartridge 102 or applied on a printed label. For example, the spring clips FIG. 4 shows a QR type 2D code 402 printed on the top surface of a cartridge 102. The internal image sensor 214 within the instrument 104 is controlled by the controller 202 to read codes printed onto the cartridge 102. Typically each cartridge code identifies the cartridge type and the corresponding diagnostic test process and analysis to be applied in processing the cartridge 102. It also typically allows the instrument 104 to read the batch or lot number and the expiry date of the particular cartridge 102. This date can be used to apply lot-specific calibrations and to exclude expired cartridges from being used in tests. This information is also included as metadata in the test result data generated by the controller 202 during the diagnostic testing.

Illumination

To assist with imaging the top surface of the cartridge 102 to read barcodes or confirm cartridge details the apparatus 104 incorporates an array of illumination Light Emitting Diodes (LEDs, not shown) arranged to provide general illumination of the cartridge 102 within the cartridge receiving port 112. These LEDs can be monochromatic such as red LEDs or may LEDs allowing a colour image to be captured by the internal image sensor 214.

Internal Reference Regions.

The instrument 104 is configured with one or more optical reference regions within the field of view of the image sensor 214 and having a known optical absorption or fluorescence. These areas can include a plain reference background with a known stable reflectivity such as 18% grey and/or printed features with known optical colour absorption properties.

Self Test Confirmation of Calibration.

The inclusion of reference regions or reference strips within the instrument 104 allows the instrument 104 to confirm the integrity of its imaging calibration within a self test function. This capability provides improved confidence and user safety in using the system 100 with the potential to have an incorrect reading or false test result as it avoids use of the system 100 if its calibration has drifted or failed.

Cartridge Construction

Figure 5:
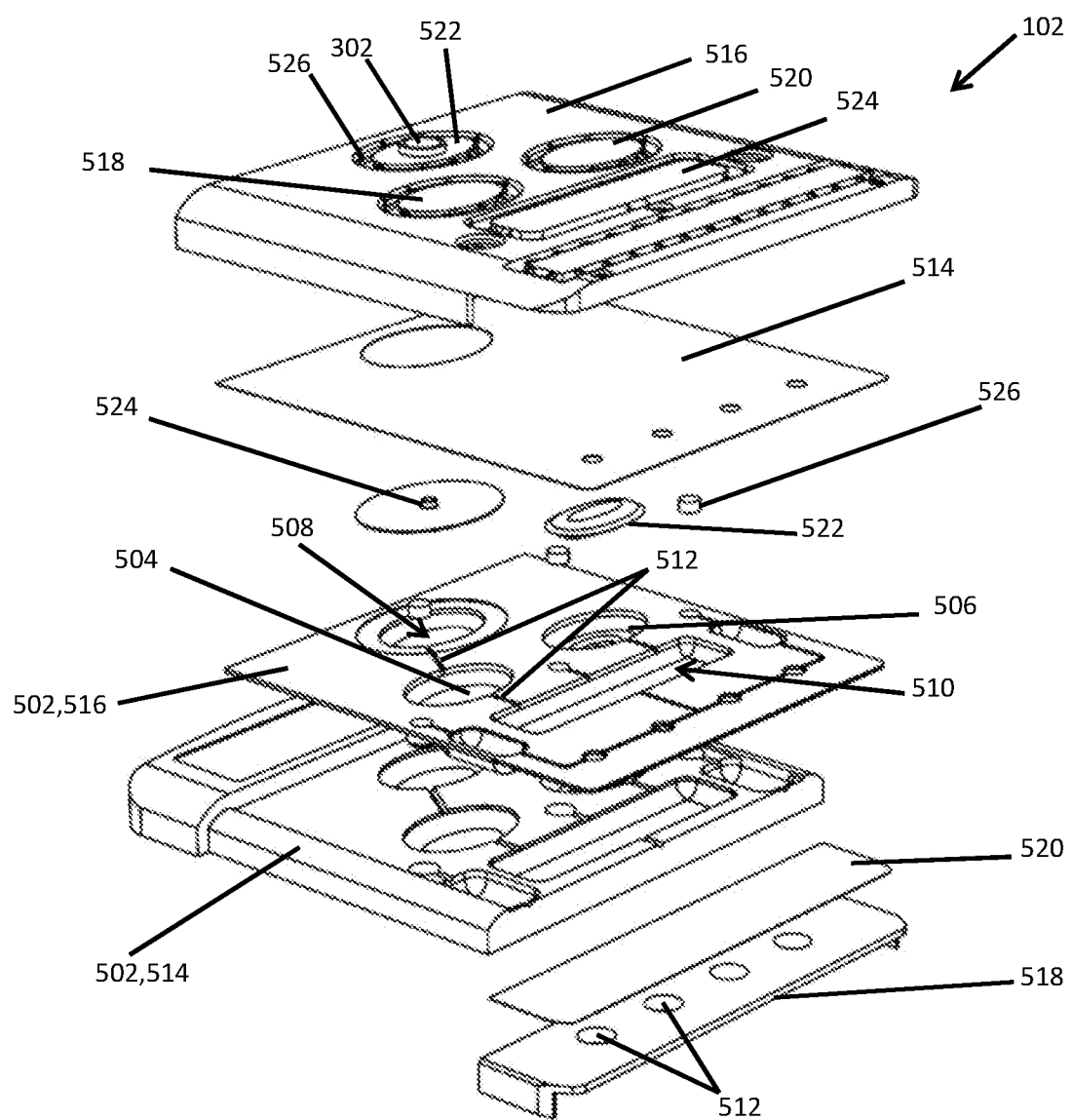

As shown in the exploded view of FIG. 5, the diagnostic test assemblies or cartridges of the system 100 each includes a substrate 502 in which are formed open reservoirs or wells 504 to 510 and open fluidic channels 512. A deformable membrane 514 is attached to the substrate 502 to cover the reservoirs 504 to 510 and the fluidic channels 512. Although the deformable membrane 514 is provided in the form of a single continuous sheet in the described embodiment, in other embodiments it can be provided in the form of a discontinuous sheet or multiple smaller sheets placed at mutually spaced locations over corresponding reservoirs and fluidic channels, with sections of rigid material bonded over channel sections where deformation is not required. Accordingly, unless the context indicates otherwise, references in this specification to "the deformable membrane" in the description and claims should be understood as encompassing all such embodiments.

A top cover 516 is disposed over the deformable membrane 514 and is configured to allow the actuators 212 of the test instrument 104 to selectively deform corresponding portions of the deformable membrane 514 in order to control the flow of liquid within the cartridge 102, as described below.

An important feature of the cartridges 102 is that they are configured so that ordinary handling by users will not affect the subsequent operation of the cartridges 102 by the test instrument 104, and this is achieved by generally inhibiting or preventing the functional deformation of the deformable membrane 514 during ordinary handling. More specifically, the cartridges 102 are configured so that human fingers are not generally able to deform the deformable membrane 514.

In the described embodiments, this is achieved in two ways, depending in part on the spatial dimensions of the portions of the deformable membrane 514 that are to be deformed. Where these spatial dimensions are sufficiently small (and are at least smaller than relevant dimensions of a human finger), the top cover 516 can be provided with simple openings in the corresponding portions of the top cover 516 above the portions of the deformable membrane 514. This because such small openings are unlikely to allow the exposed portions of the underlying deformable membrane 514 to be subjected to substantial pressures during normal handling.

However, at least where the spatial dimensions of the portions of the deformable membrane 514 that are to be deformed are sufficiently large as to pose a risk of accidental deformation during normal handling, the top cover 516 is provided with displaceable portions 518 to 524 connected to other portions of the top cover 516 by one or more corresponding deformable attachment regions 526. The deformable attachment regions 526 are configured to enable each displaceable portion to move from an initial position above deformable membrane 514 to at least one displaced position that deforms a corresponding portion of the underlying deformable membrane 514, where the displacement requires a pressure or force that is sufficiently large that it would not be applied during normal handling. For example, in the described embodiment, a force of the order of 10 Newtons or more is required to move the displaceable portions to deform the deformable membrane 514. Such large forces are extremely unlikely to be experienced during normal handling, making the cartridges 102 robust and resistant to accidental operation outside of the test apparatus 104.

Typically, the top cover 516 is provided with a combination of one or more openings (where the relevant spatial dimensions are sufficiently small) and one or more displaceable portions (where the relevant spatial dimensions are larger). For example, in the described embodiment, the cartridge 102 provides a valve to selectively prevent the flow of fluid through a fluidic channel by arranging for an actuator to press down on a corresponding portion of the deformable membrane 514 to block the fluidic channel. As the fluidic channels have a width that is smaller than the width of a human finger, it is not necessary for the valve to include a displaceable portion of the top cover 516, and therefore the valve is enabled by providing a simple opening in a corresponding portion of the top cover 516, allowing a corresponding one of the actuators 212 to directly contact and press down on the deformable membrane 514 and thus block the underlying fluidic channel.

In the embodiment shown in FIGS. 3 to 5, the open reservoirs or wells 504 to 510 include a dried reagent well 504, a liquid reagent well 506, and a mixing well 510 storing lyophilized regents, the substrate 502 also has test or amplification wells 512 in fluid communication with the mixing well 510 by way of an interconnecting channel. Views of the assembled cartridge assembly 102 are shown in FIGS. 3 and 4. The cartridge 102 is fairly small, typically having a width of about 50 mm, and a length of about 70 mm, or about the size of a business card in plan view, and the wells typically hold about 5-50 µl of fluid.

In the embodiment shown in FIG. 5, the cartridge substrate 502 consists of two components formed from respective different materials: a moulded plastic support frame 514 that supports a moulded tray 516. This configuration allows the tray 516 to be thin and use a softer plastic selected for its fluid contact properties, whereas the support frame 514 is not in contact with fluids or regents and can be formed from a stronger plastic selected for physical properties better suited to support and protection functions. For example, the support frame 514 can be formed from a strong ridged plastic such as polycarbonate, whereas the tray 516 can be formed from a plastic suitable for fluid contact or selected for its fluid contact and wetting properties such as polypropylene. The tray plastic can be a softer type of plastic and can be flexible and thin as it is supported in the assembly by the frame. However, in other embodiments, the substrate 502 can be formed as a unitary object from a single material.

The reservoirs or wells of the substrate 502 (of the tray 516 in the described embodiment) retain fluids and are also involved in the fluidic operations of the cartridge 102.

The wells within the substrate 502 or tray 516 can include at least one dried reagent well 504 that stores dried or lyophilized reagents. The wells can also include at least one liquid reagent well 506 to store liquid reagents, either directly or within a flexible package or foil blister package positioned within the well 506.

A separate part of the substrate 502 (in this embodiment, being a separate part of the support frame 514) provides a set of test wells 512 that store lyophilized reaction reagents and are where DNA amplification and genetic marker measurement occurs. The advantage of having the test wells 512 provided in a separate moulded plastic part 518 is that the part 518 can be constructed from a plastic material and surface coatings suitable to the temperatures and reactions that run within the test wells 512. Being a separate part 518, a separate processing process can be applied to add reagents and lyophilize these reagents within the test wells 518 prior to assembly of the cartridge 102. The test wells 512 can be sealed with a foil or plastic membrane 520 once its processing and reagent loading is completed such that they are protected in storage prior to assembly into an assembled cartridge 102. The plastic strip 518 with its foil cover 520 is clipped by snap fit plastic features into the end of the support frame 514 such that the fluid dispensing end of the tray 516 can sit across its top surface, thereby trapping the foil cover.

During manufacture or assembly, once the tray 516 is supported by the support frame 514, any contents (e.g., dried or lyophilized reagents) required to operate the corresponding diagnostic test are dispensed into the reservoirs of the tray 516, or alternatively these reagents may have already been dried or lyophilized in place in the tray 516, and protective foils or foils fitted over the respective wells.

Liquid reagents contained within a flexible sachet or foil capsule are placed into each well that is intended to dispense these. For example, in the described embodiment, a liquid reagent sachet 522 is placed into the reservoir or well 506.

A flexible sample input seal 524 is placed across the top surface of its associated well in the tray 516. Semi-permeable filter components 526 that allow air to pass out of venting channels but prevent liquids being released can also be added if venting of the cartridge 102 is required. In some embodiments, dedicated pressure cavities and overflow cavities are used to contain air or gasses pushed ahead by the test process with only a small increase in internal pressure and no venting of air or gas from the cartridge, thus providing a fully sealed system.

After the tray 516 is loaded with the chemical reagents and dilution liquids required for the diagnostic test processing, the flexible membrane 514 is bonded across the top surface of the tray 516. This bonded membrane 514 forms a seal over each of the wells such that only the thin channels moulded into the surface of the tray 514 form interconnecting channels between the wells.

The membrane 514 can be bonded adhesively, or it can be attached by thermal or ultrasonic welding across the top of the tray and across the set of test wells 512.

After the membrane 514 is bonded in place, openings in the membrane, such as to provide a port for sample input, may be cut and the waste membrane material removed.

Once the membrane 514 is bonded in place, the top cover 516 is clipped into place.

The top cover 516 is clipped by moulded features to the substrate 502 (i.e., to the support frame 514 in the described embodiment) such that whole assembly is rigidly retained as a unit with the tray 516 and wells captured within the assembly 102.

In addition to or as an alternative to clips, the top cover 516 can be also be adhesively bonded or thermally or ultrasonically welded to the support frame 514 and the test well strip 518 to form a unified assembly.

Cartridge Operation

Figure 6:
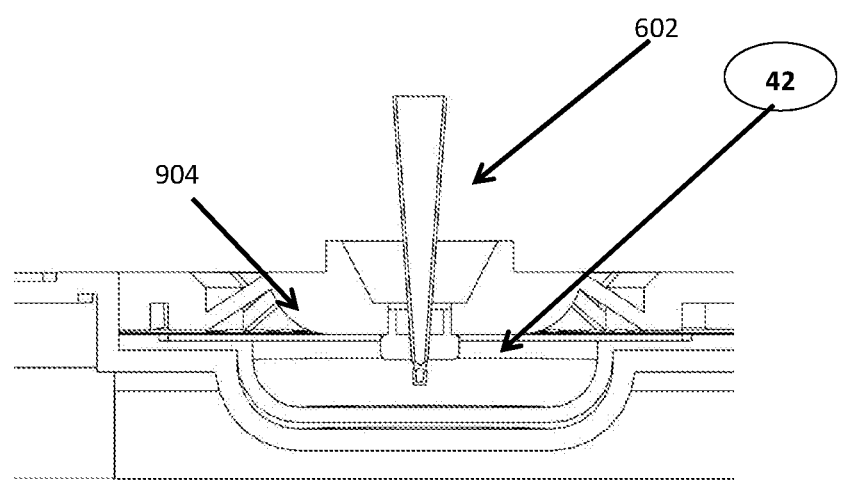
FIG. 6 is a cross-sectional view of a portion of the diagnostic test assembly or cartridge during input of a sample into a reservoir or well of the cartridge.

To perform a diagnostic test, a test sample is introduced into the sample input port 522. This process is shown in FIG. 6, where a sample applicator or pipette tip 602 is inserted into the port and pressed through the flexible elastomeric seal component 524.

A sample pipette can press through the seal 524 to introduce a given volume of sample fluid into the reservoir or well located under the sample input port. During introduction of the sample, the elastomeric seal 524 is stretched open and forms a seal around the circumference of the pipette tip. This seal component 524 is formed from a flexible material such as silicone rubber. It may be a separately moulded part that is pressed into or adhesively bonded in position during assembly of the cartridge 102.

As an alternative construction method, the flexible seal component 524 may be moulded in place in the top cover 516 using a dual moulding technique where the rigid top cover 516 is moulded first in a plastic such as polycarbonate, and the seal component 524 is moulded as a bonded part from a material such as silicon rubber in a secondary moulding operation. A fine pin withdrawn from the seal 524 provides a hole that is closed and sealed when the seal component 524 is in its resting state, but this hole allows the seal to stretch circumferentially around the pipette tip as the tip is pressed through the seal 524.

As the pipette tip is withdrawn, the seal 524 fully closes on itself and captures the sample fluid within the corresponding reservoir or well inside the cartridge.

Figure 7:
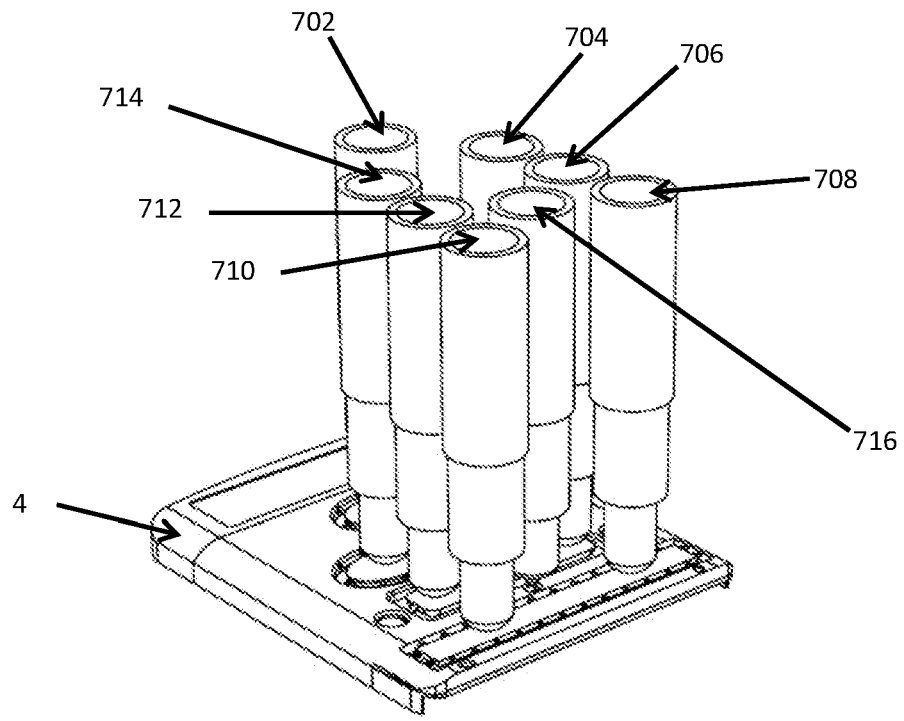
FIG. 7 shows a set of actuators of the instrument aligned with corresponding displaceable regions of the cartridge.

After the sample has been added, the cartridge 102 is fully inserted into the instrument. Once located within the instrument 104, the cartridge 102 is positioned under a set of actuators 702 to 716, as shown in FIG. 7. The actuators 702 to 716 all start in a fully raised position that allows the cartridge to be fully inserted into the instrument 104. Once the cartridge is fully inserted, the actuators can be extended down onto the surface of the cartridge under a controlled sequence to activate processes of the diagnostic test. The structure of an electrically driven actuator of the described embodiment is shown in cross section in FIG. 8.

Figure 8:
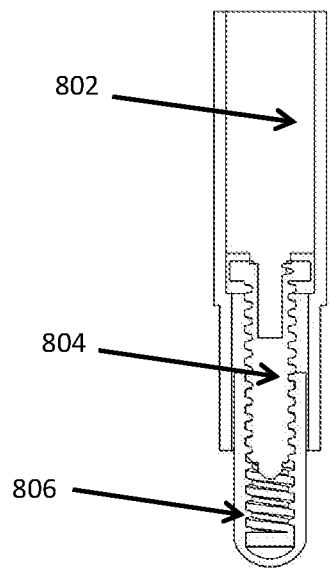
FIG. 8 is a cross-sectional view of an individual actuator of the diagnostic test apparatus or instrument.

Each of the actuators 702 to 716 includes an output shaft, an electric gear motor, and a planetary gearbox with a gear reduction of around 100:1 or greater to provide sufficient force at the output shaft. As shown in FIG. 8, the output shaft 802 rotates an attached screw 804 in a tip nut 806. If the motor is energized to operate the shaft in a clockwise direction, the nut and actuator tip 806 are withdrawn and the actuator is raised away from the cartridge surface. Conversely, if the motor is energized in a counter clockwise direction of rotation, the nut and actuator tip 806 are driven away from the motor, and the actuator will be extended and thus lowered towards and ultimately onto the cartridge surface. The actuator motor may be a brushed or a brushless type, and the electrical control to the motor can be used to stop and start the motor and to change its direction of rotation.

In some embodiments, sensors such as switches can be used to detect the extended and retracted position of the actuator and thus to prevent the motor from over extending or over retracting the actuator. However in the described embodiment, the actuator motor has a current limit that limits the maximum toque that the motor can apply. The actuator is configured with mechanical stops for its fully retracted and fully extended positions. To extend the actuator, the motor is driven in the forward position for a time that exceeds the time needed to reach the stop. The actuator contacts the stop and stalls in this position. The system is configured to have sufficient strength and the current limit is adjusted such that the assembly and its included motor can reliably withstand the stall force and not overheat or otherwise damage the motor in the stall position during the limited time that the motor is held in a stall. A similar approach is used when the motor direction is reversed and the actuator is withdrawn. This arrangement has the advantage that it sets a force limit on the actuator, and the actuator can stall once a displaceable portion of the cartridge is fully depressed prior to the inbuilt end stop being reached. This reliably actuates the cartridge without needing to accurately position or adjust end stops or end actuators. Other arrangements for building and driving an actuator that can operate a force onto the surface of the cartridge will be apparent to those skilled in the art in light of this disclosure, including the use of driven cams, lever arrangements, and the use of pneumatic cylinders. When a cartridge is fully inserted and its processing started, typically one or more actuators will press down as location clamps so that the cartridge will not move during the subsequent processing steps.

Morphological features of the cartridge such as its outside edges are locate accurately with corresponding features in a base plate of the instrument 104 that the cartridge assembly 102 is clamped against to ensure that it is well supported for the duration of the test processing.

Basic Principle of Operation

Figure 9:
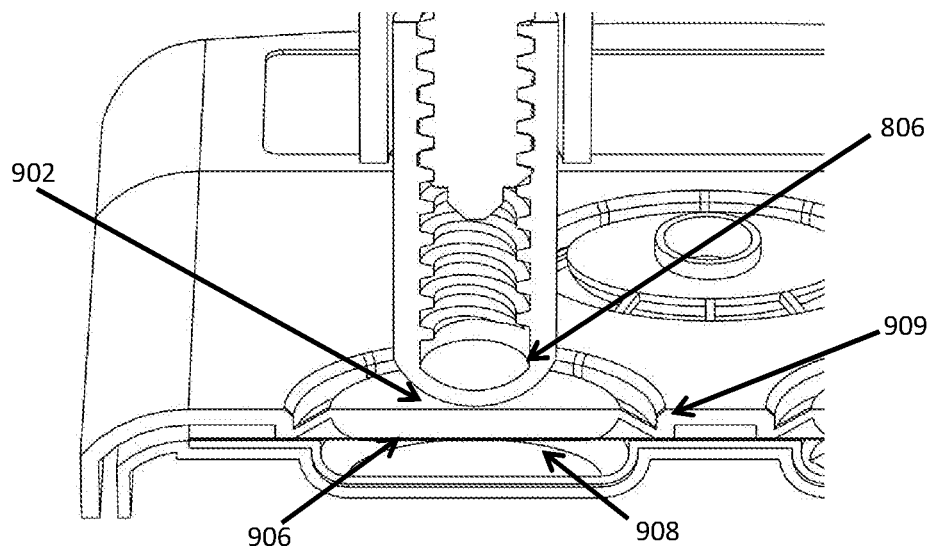
FIGS. 9 and 10 are cross-sectional views illustrating the use of an actuator of the diagnostic test apparatus to displace a corresponding displaceable region of the cartridge and thereby pump fluid from the corresponding reservoir or well of the cartridge, showing a displaceable region in its initial and displaced positions, respectively.

At least some of the displaceable portions act as pumping portions to pump or displace fluid from corresponding reservoirs through corresponding fluidic channels. As shown in FIG. 9, the top of each fluid reservoir or well 902 in the tray 516 is sealed by the covering flexible membrane 514. Fluid within the well 902 can only exit from the well 902 via a connected fluidic channel formed as a groove or open channel in the surface of the tray 516. The plastic top cover 516 protects the membrane 514 and prevents pressure on the membrane 514 during transport and storage prior to actuation in the instrument. The top cover has displaceable portions connected to the remainder of the covering by one or more corresponding deformable attachment regions. In the described embodiments, the displaceable portions are generally elliptical portions of the top cover suspended within openings in the top cover by a small number of thin and deformable support members or tabs extending across the gap therebetween. However, it will be apparent to those skilled in the art that a wide variety of alternative shapes and/or alternative forms of attachment may be provided in other embodiments and will be apparent to those skilled in the art in light of this disclosure.

In the described embodiment, the top cover is formed of a rigid plastic material, but the configuration of the support members makes them readily deformable when a corresponding displaceable portion is acted upon by one of the actuators. As shown in FIG. 9, the rigid displaceable portion 902 has increased thickness and/or reinforcing webs in its structure while the support members 904 have a reduced thickness and are thus relatively weak and easily deformed.

The underside of each displaceable portion positioned over a fluid well has a form that is complementary to the shape of the underlying well 908 and therefore displaces fluid from the well 908 when the displaceable portion 902 is pressed down into the well 908.

Figure 10:
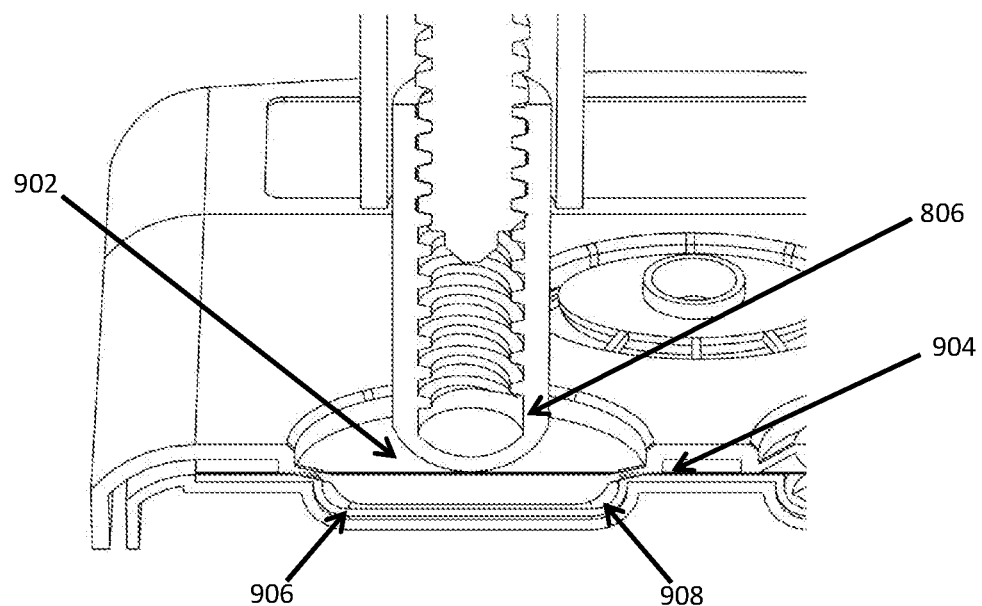

FIG. 10 shows an actuator tip 806 extended such that the deformable attachment regions 904 have collapsed or deformed and the displaceable portion 902 has compressed the underlying portion of the deformable membrane 906 into the well 908. During this action, any fluid in the well 902 will be displaced and forced to flow away through a connected channel to the next well or other form of processing stage in the cartridge 102. The membrane 906 forms the seal over the well 908 during this process. The membrane 906 has the property that it will stretch and not rupture or leak during this displacement or pumping process. The membrane 906 does not need to be elastic, and does not need to return to its original state because the cartridge 102 is not re-used and the displaceable portion 902 of the top cover is intended to stay in its depressed state once actuated. The membrane 906 may be a thin film of polyethylene or polypropylene that will stretch and deform through the top cover depression process but will retain a fluid seal and not rupture.

Clamping and Closed Valves

In the described embodiment, the actuator that corresponds with location 304 of FIG. 3 can be extended to stall with a known force against the cartridge 102. This actuation clamps the cartridge in a fixed location and holds a membrane valve in this position closed such that any fluids that enter the mixing chamber 524 cannot exit via its output channel because the covering membrane 514 is being clamped down by actuator 716 in this location and fluid low in this interconnecting channel is blocked until the actuator 716 is raised to open the valve.

Sample Progression

To progress sample fluid from the sample input chamber under the sample input port 302, the actuator 702 located over the sample input well is extended to provide additional sealing of the input port and to displace the corresponding displaceable portion into the sample input chamber to displace the sample material out of the sample input well through a connected fluidic channel to downstream processing locations on the cartridge. When this section of cartridge top cover is depressed, the sample is sealed in by the combined action of the silicon seal 524 and the actuator 702 in contact with the input port 302. As the well volume is reduced by the action of the actuator, the sample fluid is forced to exit via the interconnecting channel formed as a groove between the tray and the membrane and to flow into the next well where it can dissolve dried or lyophilized reagents placed in the well during manufacture or assembly of the cartridge.

Liquid Reagent Release

In most diagnostic tests, release of liquid reagents stored in the cartridge is required to process the sample. Typically these liquids introduce buffers or detergents to assist with cell lysis of the sample material to break down the cell walls and expose cell internals including genetic material contained with the sample for subsequent test steps and nucleic acid amplification.

Figure 11:
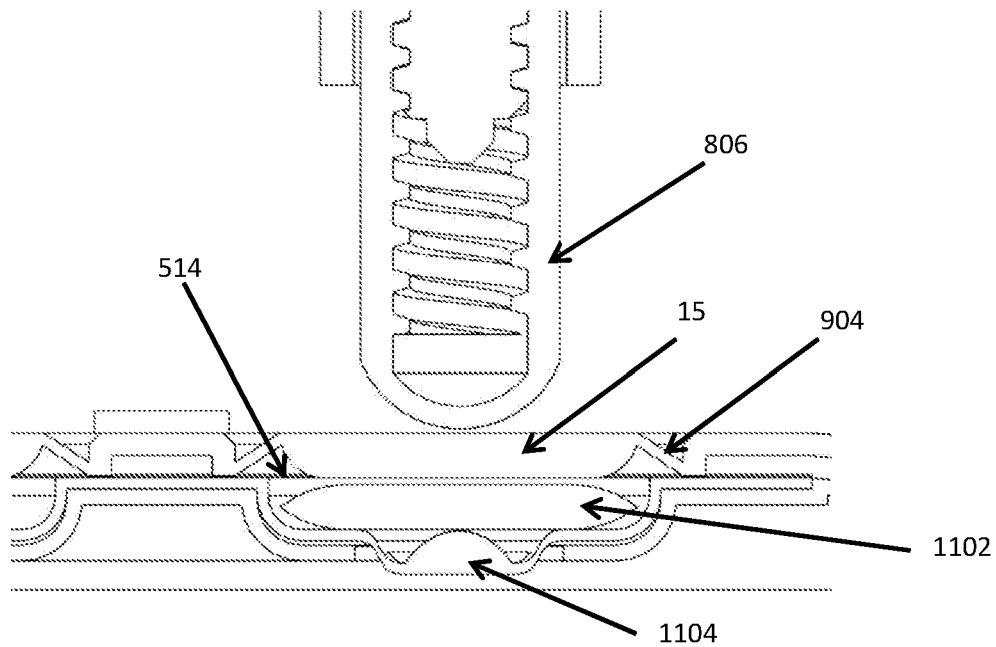
FIGS. 11 and 12 are cross-sectional views similar to FIGS. 9 and 10, but showing the release of fluid from a sachet disposed within a reservoir or well of the cartridge.
Figure 12:
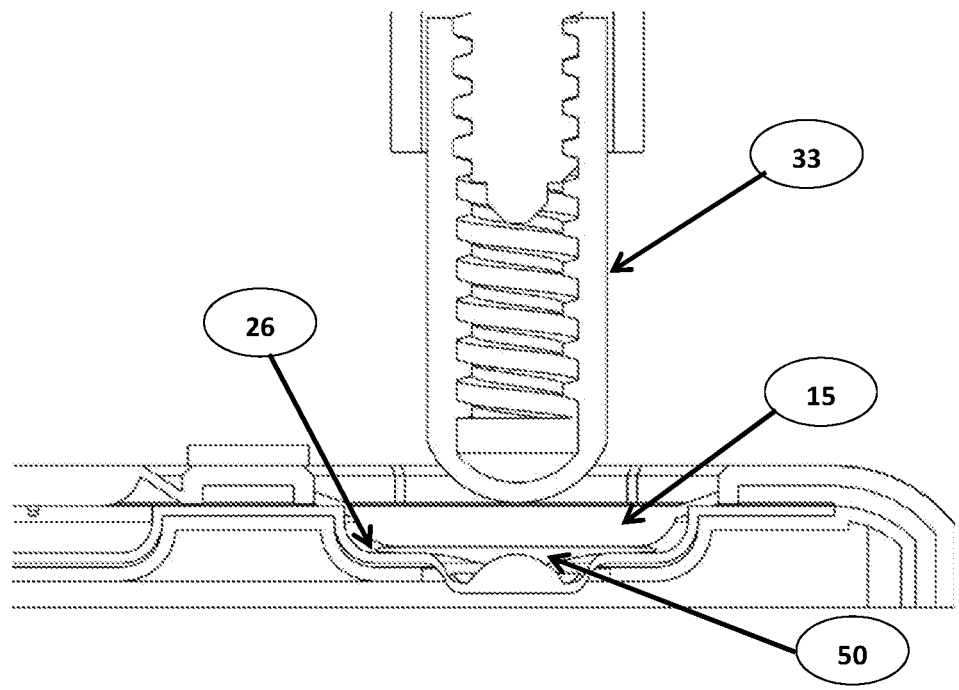

The arrangement for storage of a liquid reagent is shown in cross section in FIG. 11.

The liquid reagent is contained within a flexible sachet 1102 placed within a well in the cartridge tray 516 and subsequently sealed in place by the bonded membrane 514. When the corresponding displaceable portion 902 of the cartridge top cover 516 is acted on by the associated actuator 704 pressing down on it, the deformable attachment regions 904 deform and allow the displaceable portion 902 to deform the underlying portion of the membrane 514 when the actuator force is sufficiently high. FIG. 11 shows a liquid—containing sachet pressed against a piercing edge 1104 as the membrane 514 is pressed down against the sachet 1102 by the action of the actuator tip 806. The piercing edge 1104 will pierce or cut or the plastic membrane sachet 1102 as the actuation continues to depress the membrane into the tray depression. Once pierced, the fluid in the sachet 1102 is released and will be forced out of the sachet 1102 and also out of the enclosing well via the interconnecting channel. In the case of this cartridge, this will cause the reagent to flow into the mixing chamber 524. Sample material contained in the well 518 can also be forced out via its interconnecting channel to the mixing chamber 514 where these fluids will combine and can be mixed.

Mixing Chamber

Both sample material fluids and stored fluid reagents are combined in the mixing chamber 524, where these fluids can also dissolve dried or lyophilized materials previously placed in the chamber during the cartridge assembly process. This dry reagent material may be dried or lyophilized in place, or it can be placed into the corresponding well in the cartridge as a dry pellet or powder prior to sealing the membrane 514 over the tops of the wells in the cartridge tray 516. The diagnostic test system 100 can use two approaches to fluid mixing.

1. Magnetic Mixing.

Where magnetic mixing is utilized, one or more paramagnetic particles such as a steel ball bearing is pre-loaded and contained in the mixing chamber 524. The action of a moving magnetic field in the proximity of the well will cause the ball bearing to move through the fluid contained within the well to cause mixing. In some embodiments, the instrument 104 includes a motor driven crank that moves a permanent magnet backwards and forwards under a cartridge and in close proximity to the mixing well 510.

2. Actuator Mixing.

Figure 13:
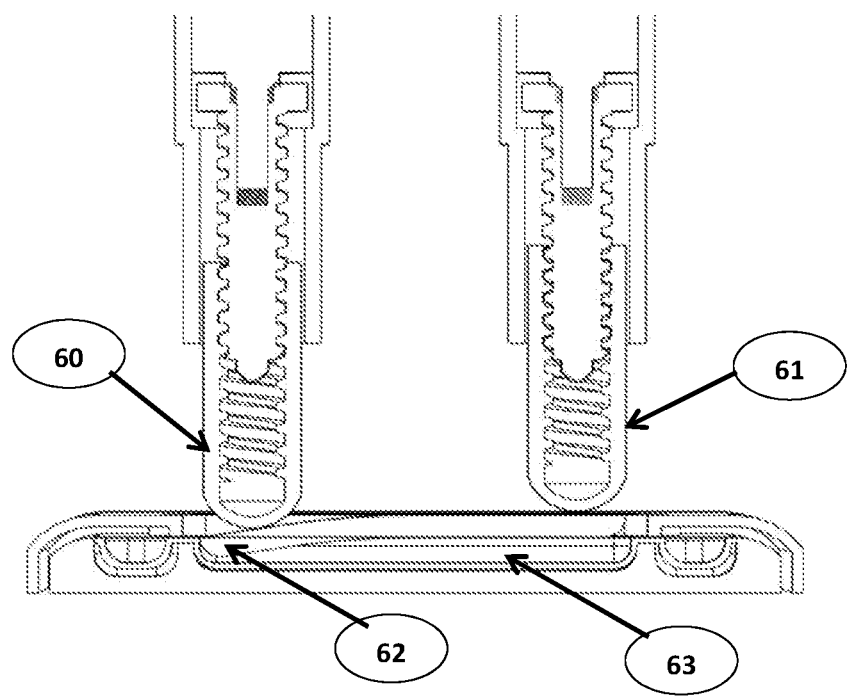
FIG. 13 is a cross-sectional view illustrating the use of a pair of actuators to alternatingly displace opposite ends of an elongate displaceable region of the hard covering to mix fluid contained within an underlying mixing reservoir or well of the cartridge.

Actuator mixing can be utilized by programming the instrument 104 to repeatedly extend and retract actuators at opposite ends of the mixing chamber 510 in an alternating manner, as shown in FIG. 13. Each of the actuators will stretch or break the deformable attachment regions (in the form of plastic tabs in the described embodiment) at the corresponding end of the elongate displaceable portion of the top cover positioned over the mixing well 524. This causes the elongate displaceable portion to pivot on the remaining central plastic tabs such that one of its ends is depressed into the elongate well and all fluid is pushed to the opposite end of the well. The fluid cannot exit the mixing chamber 510 because the previous chambers all remain blocked by their respective actuators remaining extended, and the exit interconnecting channel is blocked by actuator 716 applying pressure on the portion of the membrane 514 covering this channel at valve location 304.

This process is then reversed, where the extended actuator 60 is retracted and the other actuator 61 is simultaneously extended, causing the opposite side of the elongate displaceable portion to be depressed into the mixing cavity and the fluid contained therein to be pushed to the opposite end of the elongate well. The process of alternating actuator extensions and retractions can be repeated many times to agitate and mix the fluids and assist in dissolving any dried or lyophilized reagents also contained in the cavity or carried in the fluids. Flexible structures can be included in the reservoirs to assist with mixing by disrupting laminar flow.

Reagent Heating Prior to Amplification.

The mixing well can sit on a heated block local to only the mixing well to allow the fluid therein to be heated to a desired temperature during mixing and/or for periods prior to or after mixing. This heating step can be used to activate reagents and assist with sample preparation and cell lysis prior to dispensing the test liquids into the test wells for amplification and read out.

Filling and Sealing the Test Wells.

Figure 14:
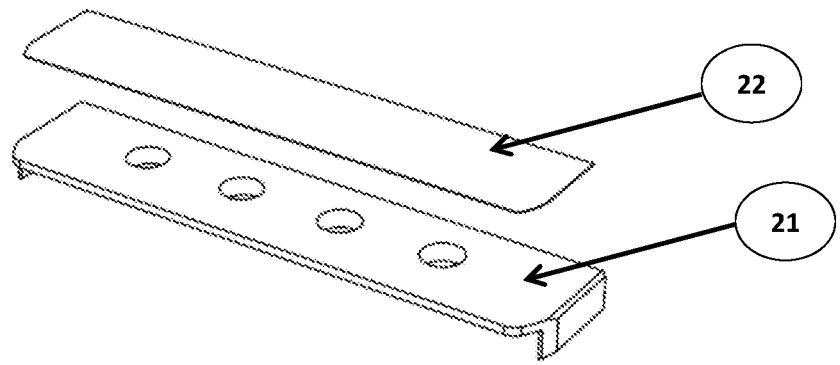
FIG. 14 is a Test well and heater block assembly—cross section.
Figure 15:
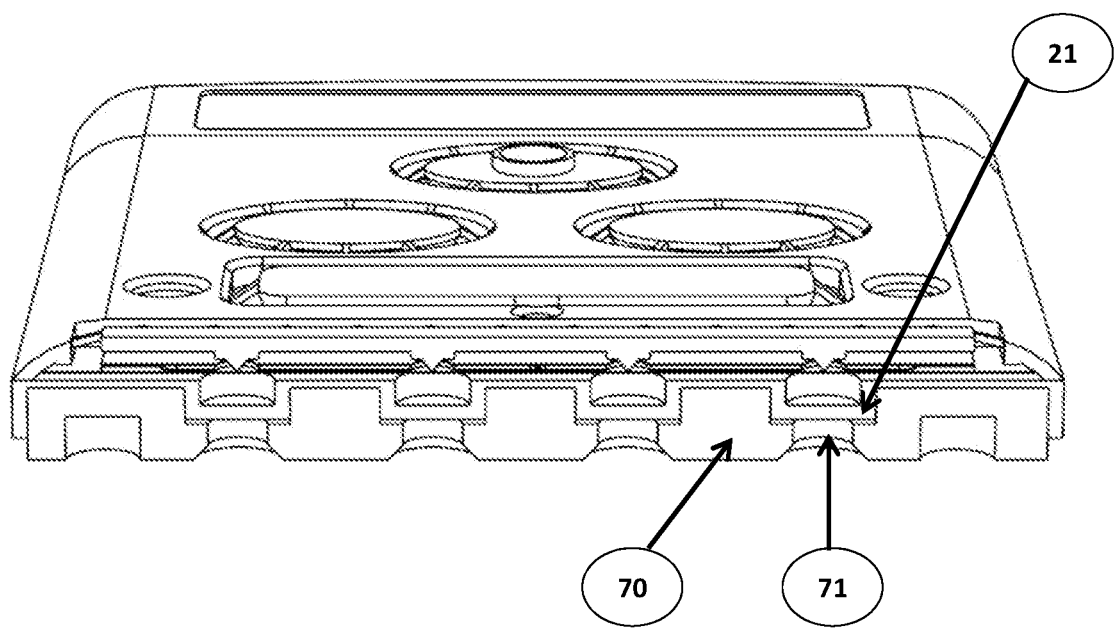
FIG. 15 is a Test well and heater block assembly—cross section.
Figure 16:
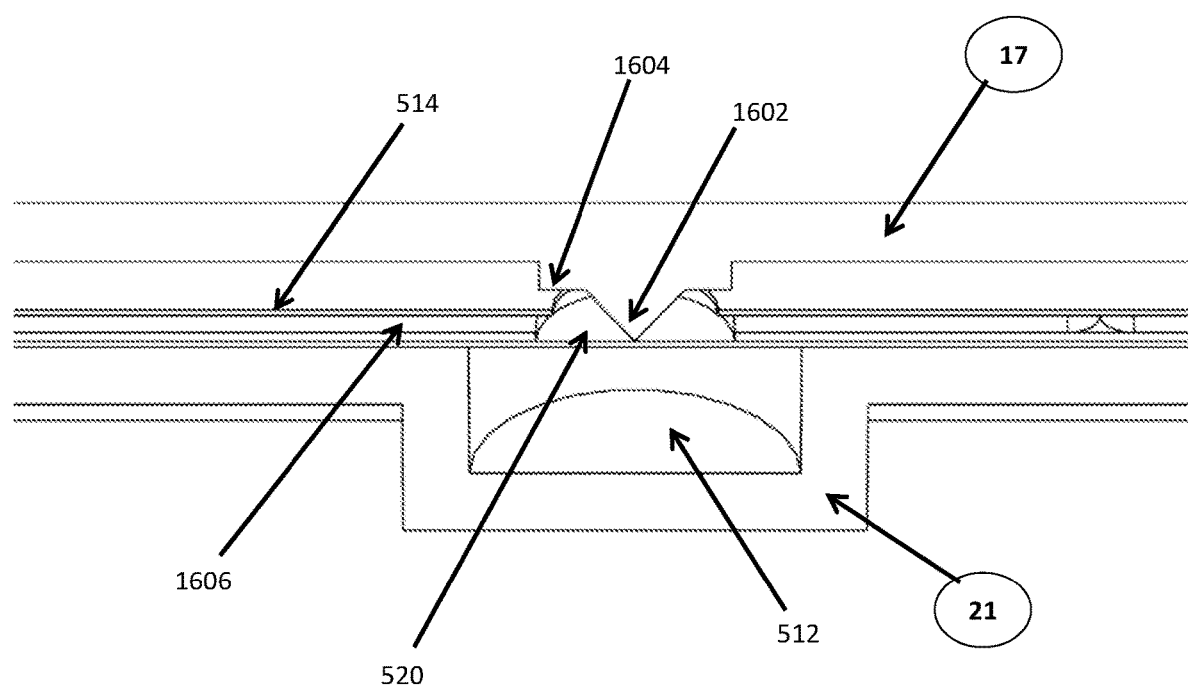
FIG. 16 is a Test well, cross section.
Figure 17:
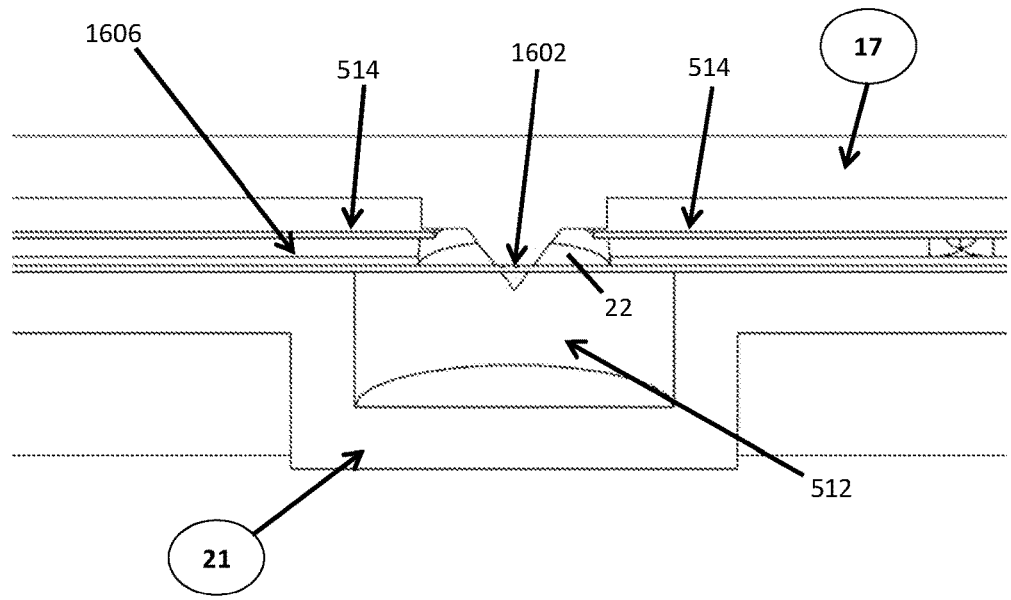
FIG. 17 is a Test well, cross section, partially depressed.

To fill the test wells, the valve actuator 716 preventing flow to the test wells 512 by applying pressure on the membrane 514 over the interconnecting channel at location 304 is lifted. Following this, both of the actuators 706 and 712 located over the mixing chamber are extended to press the entire elongate displaceable portion 524 positioned over the mixing well onto the underlying portion of the flexible deformable sealing membrane 514. This action can be controlled by controlling the rate at which the actuators are extended and will displace the fluid volume of the mixing well. This action will cause the fluid contained in the mixing well to flow through the interconnecting channel to fill each of the test wells 512 in the moulded well strip 518. FIG. 14 shows the test wells 512 in the moulded plastic will strip 518 and the covering protective foil 520 in an exploded view FIG. 16 shows an individual test well 512 in cross-section during the filling operation. The well 512 contains dried or lyophilized reagents necessary for the test assay that will enable iso-thermal or PCR DNA amplification and subsequent binding and detection of genetic markers. By only partially extending the corresponding actuators 708, 710, the displaceable portion 306 of the top cover 516 positioned over the test wells 512 is only partially depressed. This moulded plastic region has projections on its underside. FIG. 16 shows one of these projections in cross section with a piercing tip 1602 and a plug diameter 1604. FIG. 17 shows the displaceable portion 306 partially depressed such the projection tip 1602 has pierced the foil cover 520 bonded across the top over the test well plastic strip 518. By this action, a flow path is created from the groove 1606 in the cartridge tray 516 that is covered by the membrane 514 that passes by the piercing tip 1602 and through the rip in the foil cover 520 and into the well cavity 512. This flow path allows fluid displaced from the mixing chamber to flow via the interconnecting channel 1606 into the well and the overflow to be carried in the opposite side channel to the next well or subsequent wells and finally to a waste or overflow chamber. The overflow chamber can contain an absorptive pad to hold overflow liquid during the dispensing and test well filling operation.

Figure 18:
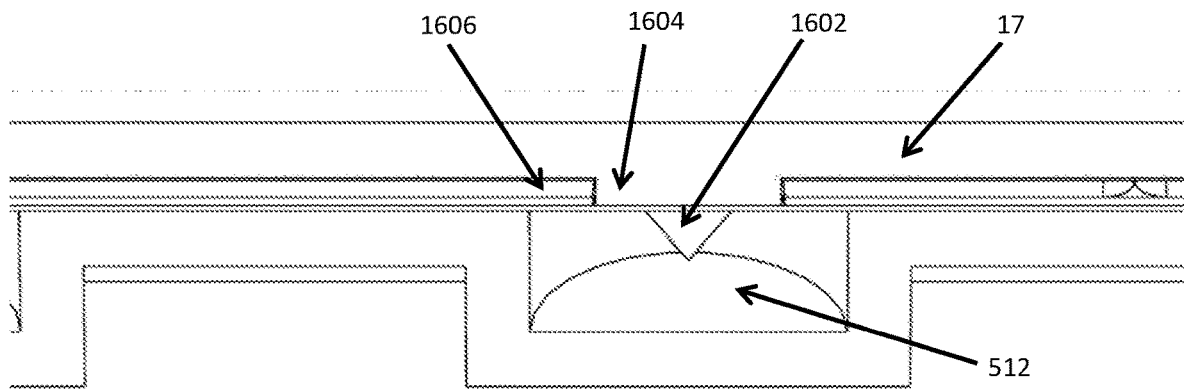
FIG. 18 is a Test well, cross section, fully depressed.

The perforation pin 1602 has a star or grooved shape in cross section to allow fluid to run past the perforated foil cover 520 into the well 512. The fluid displaced down the channel 1606 can flow into and fill the well 512. Excess fluid can then flow across the top of the well 512 and out a second interconnecting well to a waste or overflow volume. When the fluid dispensing is completed the plungers 708, 710 are fully extended by the instrument controller to completely seal the filled test wells 512. FIG. 18 shows a completely filled and sealed test well in cross-section. The actuators 708, 710 are fully extended and the plug diameter section 1604 forms a plug seal in the aperture in the tray and seals the test well 512.

Sealing of the Test Wells Prior to Amplification or Test.

The plug section 1604 in FIG. 18 is configured to be a tight friction fit and to lock into place such that after the actuators are all lifted and the cartridge is removed, the contents of each test wells will remain fully closed. The displaceable portion of the top cover that is depressed onto the test well section may include additional plastic clips to assist with ensuring it will remain locked down once the test wells are pressed shut and all actuator force is removed. This is an important advantage of the cartridge configuration, as it prevents escape of genetic material or amplicons from the test wells after the test is complete and amplification has taken place. Any release of this amplified genetic material into the instrument or surroundings after a test could contaminate the instrument or its surrounding and cause false test results in subsequent tests.

Fluid Flow Detection.

The fluid reagents stored in the cartridge can be coloured with a dye. If the test is detected using fluorescence, the fluid reagents such as the sample lysis buffer stored in the blister pack 1102 can have a coloured, non-fluorescent dye added. This dye can be used by the image sensor to visually image coloured or contrasting fluid flow in sections of the cartridge. As shown in FIGS. 3 and 4, window openings 308 in the top cover 516 are located over the overflow wells in the cartridge tray. These overflow wells are sealed by the covering membrane, which is optically transparent to allow imaging through the membrane. The addition of coloured dye to the fluid improves contrast in the resulting images, and the window openings 308 facilitate entry of the coloured reagent fluid to be detected by the image sensor. In some embodiments, at least one of the underlying support frame 514 and the top cover 516 is also optically transparent to facilitate imaging of the fluids in the diagnostic test assembly 102.

Temperature Control or Temperature Cycling.

The actuators 708, 710 are typically maintained in an extended position for the duration of the test to ensure the section 17 of the top cover is held down and the test wells are sealed. This action also ensures that the test wells are firmly clamped against the heater block on the underside of the cartridge during the amplification and measurement section of the test process.

Alternatively, an air cavity maintained at a fixed temperature by recirculation within an external cavity that envelops the test wells can be used to control the temperature in the test wells. Using either of these temperature control methods, the test wells are maintained at a fixed temperature for isothermal DNA amplification or are cycled between several temperatures for PCR type DNA amplification.

Figure 19:
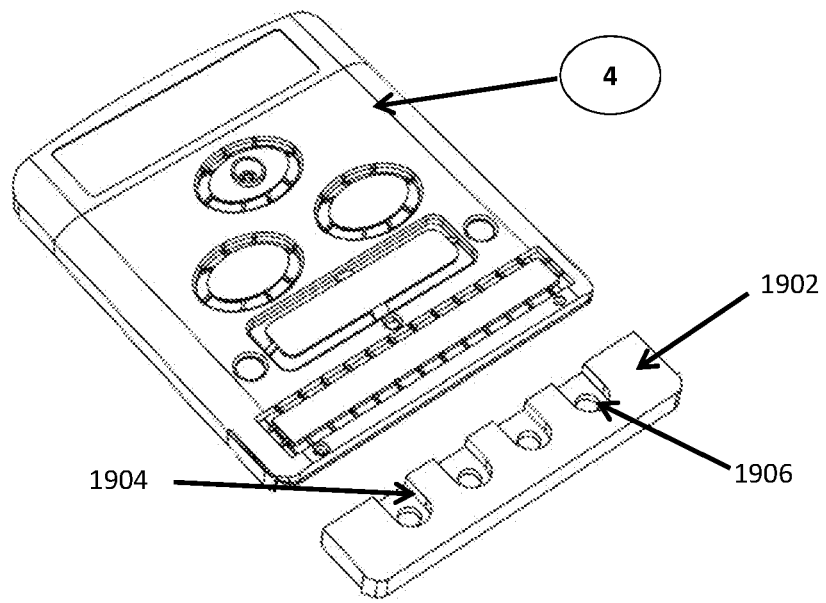
FIG. 19 is a Heater Block, cartridge not fully inserted.

FIG. 19 shows the cartridge assembly 102 partially inserted into the test well heater block 1902. The heater block is a thermally conductive block manufactured from a thermally conductive material. In this embodiment the block is an anodized aluminium component, but other suitable materials include copper or titanium. When the cartridge is placed into the heater block, the test wells projecting down from the underside of the cartridge slide into corresponding slots 1904 in the heater block 1902, as shown in FIG. 19. The block 1902 is in close thermal contact with the test wells during the test and is also clamped in place by extended actuators. The temperature of the heater block is controlled by the instrument controller, which provides either constant temperature or cycling temperature conditions within the fluid filled wells for iso-thermal or PCR type DNA amplification. The heater block 1902 incorporates optical ports of which 1906 is one port such that a set of sensors can stimulate and measure optical signals from the well contents through the optically transparent base of the test well.

Figure 20:
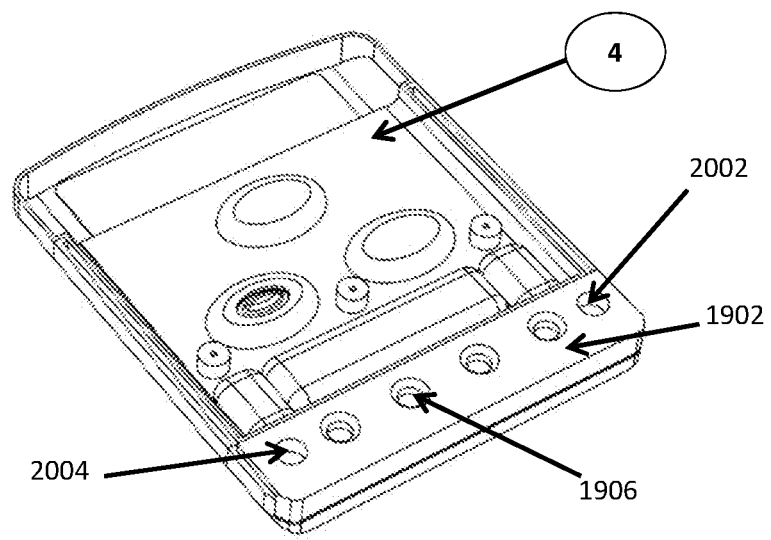
FIG. 20 is a Heater Block in position on the cartridge, underside view, showing optical ports and reference sample locations.

FIG. 20 shows an underside view of the test cartridge 102 with the heater block assembly 1902 in place. This view shows the optical ports in the heater block that provide optical access for the sensors to the transparent bases of the test wells. The additional cavities 2002, 2004 contain reference targets for instrument calibration self-test. With this arrangement, the test chemistry in the test wells provides a fluorescence output as the test output signal, and the reference samples are clear plastic inserts that have been moulded with a low concentration of inorganic fluorescing dye to provide a stable reference signal within the sensitivity range of the optical sensors. These reference sample plastic inserts are arranged in line with the test wells such that the same sensor scanning process used to move the sensors across each of the test wells can also move the sensors to positions where the properties of the reference samples can also be measured. The reference samples are mounted within mounting cavities in the heater block 1902 so that their fluorescent or optical properties can be measured at a known controlled temperature, as these properties, in particular fluorescence, can change with temperature.

Self Test Confirmation of Calibration.

The instrument apparatus 104 includes provision for internal reference samples to be incorporated within the reading area. These are shown in FIG. 20 located in the insert locations 2002 and 2006. These reference materials can be read for their optical properties such as fluorescence during the same measurement scanning process used to read the optical properties of the test wells. These reference samples are typically small moulded or cast plastic components manufactured to have known stable optical properties. In general, one or more references may be included and these are typically manufactured from a clear plastic material doped with coloured or fluorescent materials to create known stable optical properties.

During the manufacture of the instrument or subsequent service or calibration of the instrument, the optical properties of the reference samples are measured and measurement values recorded to non volatile internal memory. In subsequent diagnostic tests, the internal references can also be measured in addition to measurements of the cartridge test wells 512. The reading values of the reference samples can then be compared with the previously measured values saved in the instrument's non-volatile memory, and if they are within a pre-determined tolerance, say + or −10% of the reading value, then the test readings are deemed valid, and the instrument will continue to a test result.

However, if the readings are out of tolerance, a warning or error can be displayed to the user, and the generation of a potentially erroneous test result avoided.

The inclusion of the reference regions within the instrument allows the instrument to confirm the integrity of its measurements and calibration within a self test function.

This self test function can also be run without a cartridge inserted as a self test such that the instrument can confirm its measurement integrity before the user starts a test and inserts a cartridge.

This capability provides improved confidence and user safety in using the system with the potential to have an incorrect reading or false test result as it avoids use of the system if its calibration has drifted or failed.

Test Readings.

Figure 21:
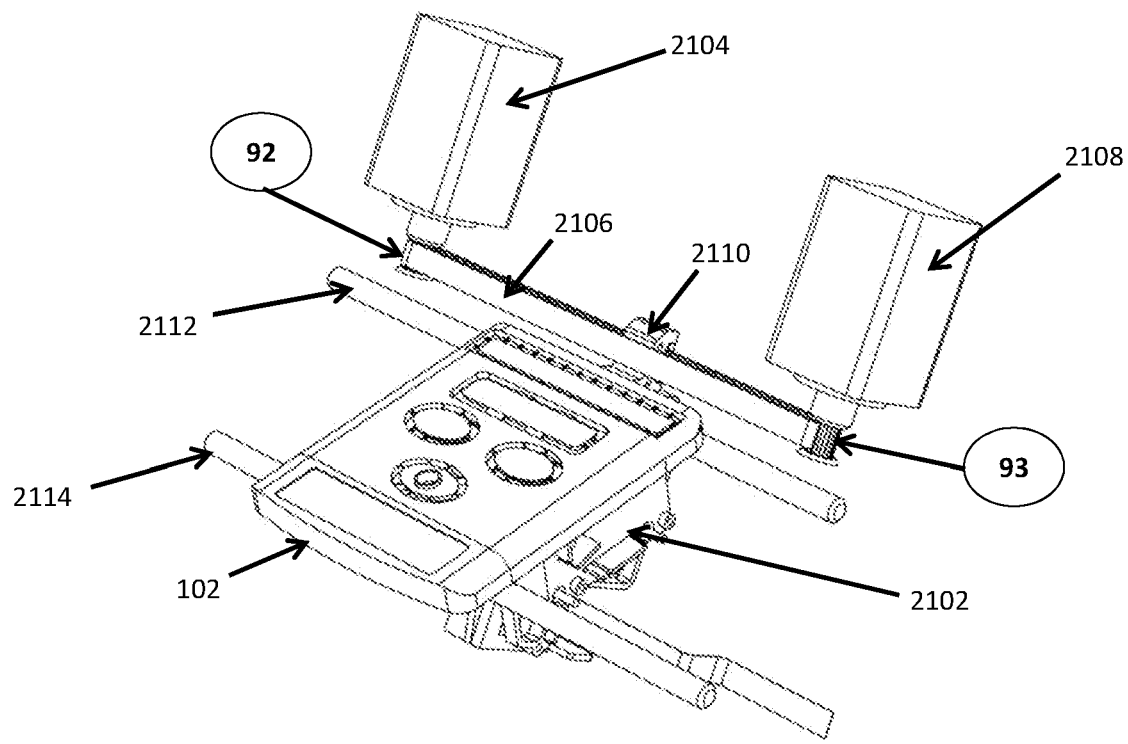
FIG. 21 is an Optical Sensors, linear carriage, scanning arrangement.
Figure 22:
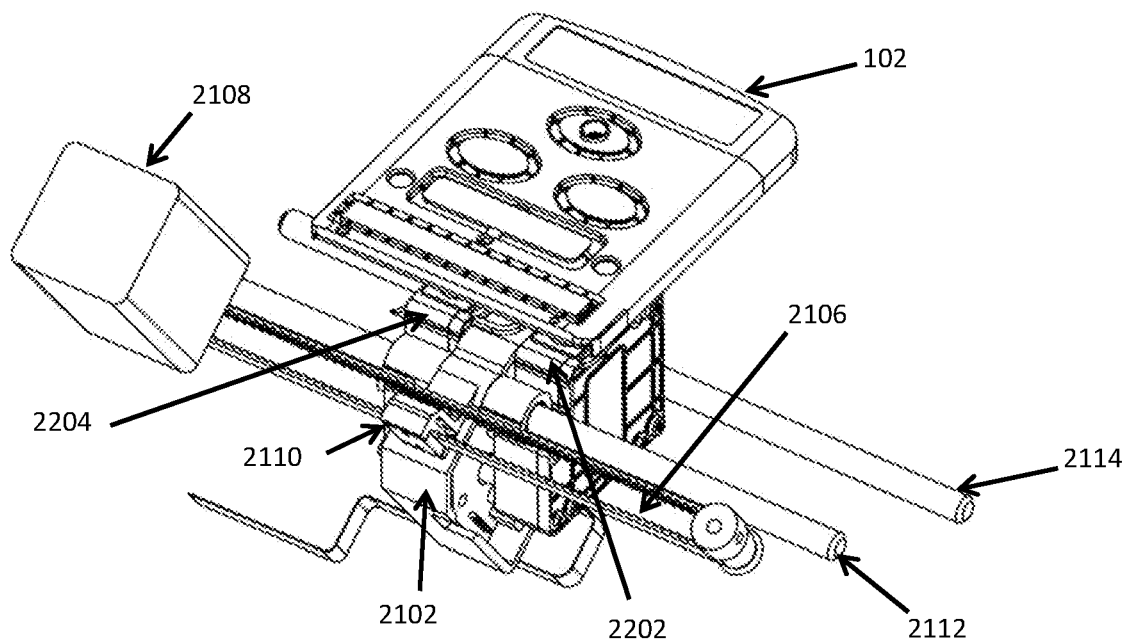
FIG. 22 is an Optical Sensors, linear carriage, scanning arrangement

While the amplification is running, test readings are taken by optical sensors that can view the contents of the test wells through holes in the heater block and corresponding optically transparent sections on the test wells. The optical measurements are taken through the flat underside of the flat bottom test wells. These measurements can use optical absorption, florescence emission or bioluminescence emission to detect specific biological or genetic sequence markers in the test wells. The measurement arrangement for this is shown in FIGS. 21 and 22. A carriage 2102, has one more sensor modules 2202 and 2204 mounted to it frame.

The carriage 2102 and attached sensors are moved by a positioning motor such as a stepper motor 2104 driving a toothed belt 2106. The belt 2106 is supported on drive pulleys mounted on the shaft of the motor 2104 and an idler shaft and bearings 2108. The sensor carriage is attached to the belt at a point by the clamp 2110. Under the action of the drive motor 2104 moving the toothed belt, the carriage is caused to move by sliding along linear polished bars 2112, 2114.

This arrangement can move the sensors 2202, 2204 such that they successively align with the underside of each test well in the cartridge 102. This scanning movement can be used to acquire measurements for each sensor at each test well. This scanning process can be a sequence of moves where each sensor is positioned and stopped in line with each test well in turn. At each position, a set of test measurements is taken. At the completion of a set of moves and measurements, the carriage can be moved back to its starting position and the scanning process repeated.

An alternative sensor scanning arrangement is to move the carriage at a constant speed so that the carriage and the sensors it carries are moved across the sensing window of each of the test wells at a constant speed. A continuous series of measurements are then acquired during this constant speed scanning move.

This signal is made up of many measurements and once acquired, the controller can locate the peaks that correspond with each test well 512. These peak or maximum points correspond with the well optical signal and are a similar measurement to that which would have been acquired if the sensor was accurately stopped at each well location with the sensor aligned with the optical widow through the heater block and test well. The advantage of the moving acquisition method, without stopping to acquire measurements at each well location, is that the carriage does not need to stop for each measurement and therefore the overall scanning time and measurement repetition rate for each test well can be much improved. This then allows a higher measurement sampling rate for each test well. In many applications the test outcome is determined by the dynamics of the reactions in the test well, and a series of measurements needs to be acquired at an adequate sample rate while the test is running to have the data needed for analysis and subsequent determination of the test outcome.

Alternative Measurement Methods

Although the description above refers to optical measurements of the test well to determine a test result, it is recognized that sensors with alternative measurement methods can operate in the same apparatus and test cartridge described herein. These sensors may use magnetic, electrical, atomic or physical properties of the test fluids to acquire measurement suitable to determine a test result.

Test Well Mixing

In some diagnostic testing, mixing of the contents of the test well is necessary for the test to run correctly or to improve the test reliability or accuracy.

To achieve mixing, paramagnetic particles such as small steel ball bearings are included in the test wells during reagent loading of the test wells and prior to bonding the foil protective cover. In this configuration, permanent magnets are fitted to the sensor carriage such that as the carriage traverse passes each of the test wells a magnet fitted high will lift the particles and they will subsequently fall back to the base of the well under gravity after the carriage has passed. Alternatively, high and low magnets can be fitted to pull the mixing particles or balls to alternate positions in each well as the carriage passes. This movement of the mixing ball within each well induces mixing in the well fluid. This arrangement also has the advantage that it can be configured to pull the included particles or ball to a preferred position when each sensor is close to the well such that these particles do not interfere with the optical measurements of the well contents.

UV Denaturation

The diagnostic test system 100 incorporates ultraviolet illumination in the cartridge receiving port 112 that can be turned on or off by the instrument controller. This illumination can be an illumination of the entire cartridge, or implemented as a localised source within the scanning head to denature the amplified contents of the test wells as the scanning arrangement moves past the test wells. This UV illumination is used to denature and sterilize the contents of the cartridge in particular to denature any amplified genetic, nucleic acid material, referred to as amplicons.

A specific component of the described diagnostic test system 100 is a high intensity ultra violet light emitting diode also mounted on the carriage of the scanning measurement head 2114 shown in FIGS. 21 and 22. This Ultraviolet LED can also include focusing optics to concentrate the UV light onto a high intensity localised region that can be directed to each test well in turn by the scanning mechanism. This high intensity UV illumination will illuminate the liquid volume of each test well and denature any nucleic acid amplicons present in the test well at the completion of amplification and test result detection. The carriage can be scanned as a continuous movement, or it can move and stop at each well. By either method, high intensity UV illumination is applied to each test well in sequence. The UV illumination level and the exposure duration is configured by the controller to ensure that the DNA genetic amplicon contents of each well are completely denatured and will not undergo further amplification in the event that the test well contents were to be released and introduced into another test.

This denaturing of the test well contents can also be achieved or enhanced by operating the test well heater at an elevated temperature such as 100° C. for a period of time sufficient for the genetic material in the test wells to be broken up and denatured within the test well solution. The combination of increasing the temperature of the test wells using the heater block under instrument control and applying UV illumination can be used to optimize and increase the efficiency of the breakdown and destruction of the genetic nucleic acid material within each test well 512.

End of Test Releasing the Cartridge

Once a test has completed and the ultraviolet post treatment completed, the instrument 104 will advise the user on the front panel LCD display 108 that the test is completed and the cartridge 102 can be removed from the instrument 104. To allow the cartridge 102 to be removed, all of the actuators are disengaged from the cartridge 102 by the instrument controller. In an alternative arrangement, an additional actuator ejects the carriage from the cartridge receiving port 112 to assist the user in removing the cartridge for disposal at the completion of the test.

Figure 24:
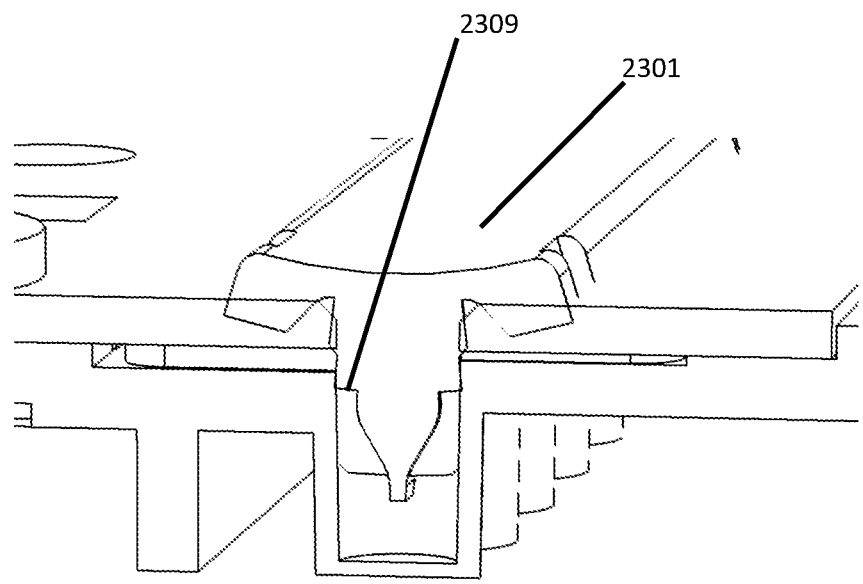
Figure 25:
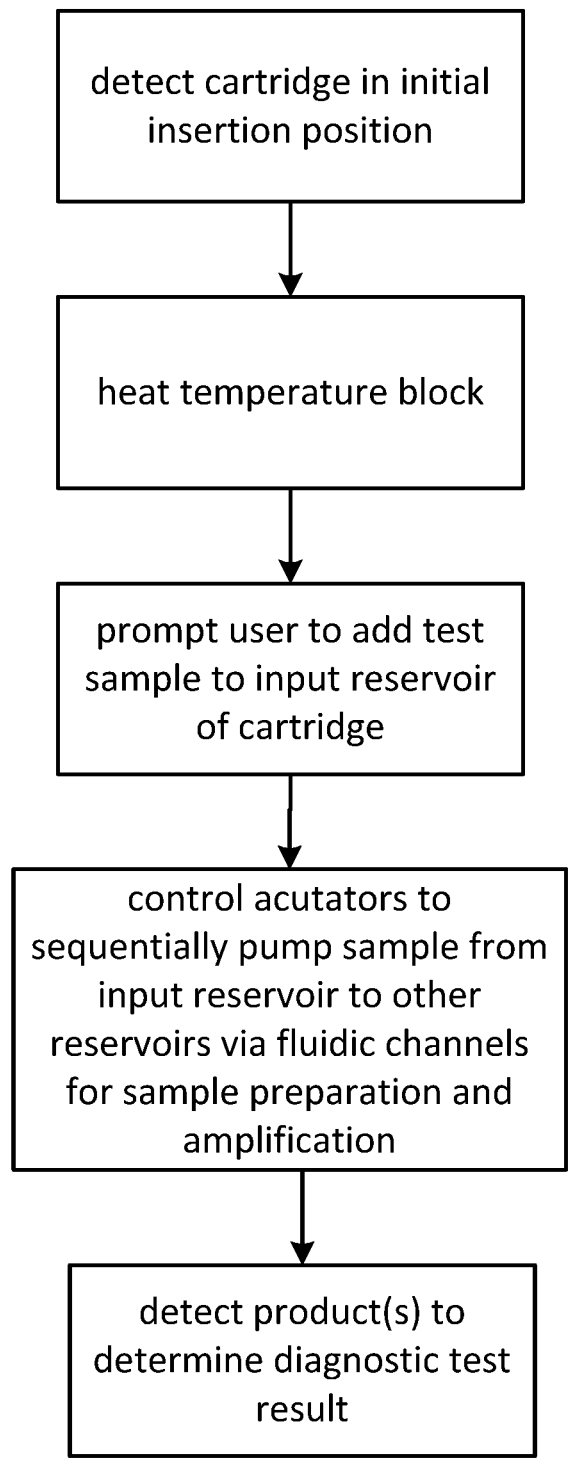
FIG. 25 is a flow diagram of a diagnostic test process executed by the diagnostic test apparatus.

In some embodiments, as shown in FIGS. 23 and 24, a deformable plug or cap component 2301 fitted over the test wells 2302 is a moulded elastomer part such as a moulded silicon body. A number of test wells are formed into the moulded plastic tray 2303, where the tray has a rigid cover slide 2304 fitted. The cover slide 2304 forms an input channel 2305 and an output channel 2306 into and out of each test well. Fluid displaced from a reservoir within the cartridge can flow into the well, through the input channel 2305 and fill the well. A projection or tab 2307 projecting from the central plug 2308 of the deformable component forces the fluid to flow down into the well while air is displaced out of the outlet channel 2305. This arrangement prevents the capture of air bubbles in the test well 2302 during filling.

The outlet channel 2306 has a much smaller cross sectional area than the input channel 2305 such that it allows air to be freely expelled from the well while it fills, but the pressure required to continue pushing test liquid from the outlet increases significantly once the test liquid reaches the outlet channel 2306. This arrangement allows a set of test wells operated in parallel to all fill prior to fluid being pushed out of any of the well outlets. Once the test liquid starts to flow out of any of the outlets, all of the wells 2302 being filled in parallel will be already full with test fluid.

Once the test wells 2302 are filled, one of the actuators of the test instrument is controlled by the controller to apply pressure to the top of the deformable component 2301, and this action forces the widest section 2309 of the deformable plug 2308 down into the well, as shown in FIG. 24, to cause the input and output channels 2305, 2306 to be sealed and a fixed volume of test liquid to be sealed within the test well 2302. This captured and sealed test liquid volume within the test well 2302 can then be processed using the heating, amplification and detection stages of the test process.

Many modifications will be apparent to those skilled in the art without departing from the scope of the present invention.

What is claimed is:

1. A diagnostic test assembly, including:
a substrate having formed therein a plurality of mutually spaced open reservoirs and fluidic channels;

a deformable membrane attached to the substrate to cover the open reservoirs and fluidic channels;

a rigid covering disposed over the deformable membrane, the rigid covering being configured to allow respective independently operable actuators external to the diagnostic test assembly to displace corresponding portions of the deformable membrane;

wherein at least some of the portions of the deformable membrane act as pumping portions, each pumping portion being disposed over a corresponding one of the reservoirs and being configured so that when it is displaced by a corresponding actuator, it is displaced into the corresponding reservoir to pump fluid from the corresponding reservoir through at least a corresponding one of the fluidic channels; and wherein one or more of the portions of the deformable membrane act as respective valve portions, each valve portion being configured so that when a force is applied to the valve portion by a corresponding actuator, the deformable membrane blocks fluid flow through a corresponding reservoir or fluidic channel; and wherein movement of fluid within the diagnostic test assembly can be controlled by controlling the independently operable actuators to control displacements of the portions of the deformable membrane such that selective displacements of one or more selected ones of the one or more valve portions define respective different flow paths through one or more corresponding ones of the fluidic channels, and selective displacements of one or more selected ones of the one or more pumping portions pumps fluid along a corresponding flow path defined by the one or more displaced valve portions.

2. The diagnostic test assembly of claim 1, wherein the rigid covering disposed over the deformable membrane has openings through which the external actuators can pass to apply pressure to corresponding portions of the deformable membrane.

3. The diagnostic test assembly of claim 1, wherein the rigid covering has displaceable portions connected to other portions of the covering by one or more corresponding deformable attachment regions, each said displaceable portion being displaceable to move from an initial position to at least one displaced position that correspondingly deforms a corresponding portion of the deformable membrane.

4. The diagnostic test assembly of claim 1, wherein the reservoirs include a sample input reservoir configured to receive a sample for analysis within the diagnostic test assembly.

5. The diagnostic test assembly of claim 1, wherein at least a first one of the reservoirs contains reagents for sample preparation including cell lysis, and at least a second one of the reservoirs is configured for nucleic acid amplification and binding of specific markers to provide an optical output that can be measured by one or more sensors external to the diagnostic test assembly to determine a diagnostic test result.

6. The diagnostic test assembly of claim 3, including a plurality of test reservoirs containing dried or lyophilized test reagents, wherein the displaceable portions of the rigid covering include test reservoir displaceable portions configured to disrupt seals of the test reservoirs when moved to respective first displaced positions to allow fluid to flow into the test reservoirs from at least one corresponding fluid channel, and to then seal the volume of fluid contents within the test reservoirs when moved to respective second displaced positions.

7. The diagnostic test assembly of claim 6, wherein at least one of the test reservoirs contains a sealed sachet of liquid, and the corresponding displaceable portion of the rigid covering is configured to disrupt the sachet to release the liquid into the test reservoir when the corresponding displaceable portion is moved into the test reservoir to a displaced position.

8. The diagnostic test assembly of claim 7, wherein the corresponding displaceable portion of the rigid covering is configured to disrupt the sachet to release the liquid into the test reservoir when the corresponding displaceable portion is moved to a first displaced position, and to seal the test reservoir when moved to a second displaced position.

9. The diagnostic test assembly of claim 6, including a deformable plug or cap disposed over a test reservoir, and configured to redirect fluid entering the test reservoir towards a base of the test reservoir to inhibit bubble formation or capture in the test reservoir during filling of the test reservoir.

10. The diagnostic test assembly of claim 6, wherein the fluidic channels include at least one input channel for filling the test reservoirs and at least one output channel to receive fluid from the test reservoirs, at least one spatial dimension of the at least one output channel being smaller than at least one spatial dimension of the at least one input channel such that fluid flow from the test reservoirs to the at least one output channel is effectively inhibited until the test reservoirs have been filled.

11. A diagnostic test apparatus, including:
the diagnostic test assembly of claim 1;
a controller; and
a plurality of independently operable actuators configured to selectively displace the corresponding portions of the deformable membrane under control of the controller to selectively control the movement of fluid within the diagnostic test assembly.

12. The diagnostic test apparatus of claim 11, wherein the controller is configured to cause at least one of the actuators to repeatedly displace a corresponding portion of the deformable membrane between first and second positions and thereby to cause mixing of contents of a corresponding reservoir of the diagnostic test assembly.

13. The diagnostic test apparatus of claim 11, including a heater block configured to heat the test reservoirs within the assembly for iso-thermal or thermo-cycling PCR nucleic acid amplification.

14. The diagnostic test apparatus of claim 11, including one or more image sensors configured to generate image data representing one or more images of at least one portion of the diagnostic test assembly, wherein the images represent at least one of: (i) at least one identifier that identifies the diagnostic test assembly; and (ii) the fluid distribution within at least some of the channels and reservoirs to allow the controller to monitor, confirm or control the status and action of cartridge actuations.

15. The diagnostic test apparatus of claim 14, wherein the at least one identifier identifies a corresponding diagnostic test to be applied to the diagnostic test assembly and determining at least one of the actuation of the actuators and the thermal processing of one or more of the reservoirs.

16. The diagnostic test apparatus of claim 11, including one or more optical sensors configured to generate optical data representing optical absorption or emission by a sample in one or more of the test reservoirs.

17. The diagnostic test apparatus of claim 16, wherein the one or more optical sensors are mounted to a translation stage under control of the controller so that the optical sensors can measure optical absorption or emission from selected reservoirs of the diagnostic test assembly.

18. The diagnostic test apparatus of claim 11, including at least one ultra violet (UV) emission source as a denaturing component configured to denature samples contained within the diagnostic test assembly following a diagnostic test to inhibit contamination in the event of sample fluid escaping from the diagnostic test assembly.

19. A diagnostic test process, including:
receiving the diagnostic test assembly of claim 1;
selectively displacing each of the portions of the deformable membrane to a corresponding displaced position to selectively pump fluid through reservoirs and fluidic channels of the diagnostic test assembly to test reservoirs of the diagnostic test assembly for analysis.

* * * * *